US012685462B2

(12) United States Patent     (10) Patent No.:   US 12,685,462 B2

Park et al.     (45) Date of Patent:     Jul. 21, 2026

(54) ELECTRONIC DEVICE AND METHOD FOR CONTROLLING SENSOR

(71) Applicant: Samsung Electronics Co., Ltd., Suwon-si (KR)

(72) Inventors: Minho Park, Suwon-si (KR); Younghyun Kim, Suwon-si (KR); Joongwoo Ahn, Suwon-si (KR); Jeahyuck Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 149 days.

(21) Appl. No.: 18/739,966

(22) Filed: Jun. 11, 2024

(65) Prior Publication Data

US 2024/0415425 A1     Dec. 19, 2024

Related U.S. Application Data

(63) Continuation of application No. PCT/KR2024/007875, filed on Jun. 10, 2024.

(30) Foreign Application Priority Data

Jun. 13, 2023    (KR) ........................ 10-2023-0075486
Jul. 19, 2023    (KR) ........................ 10-2023-0093826

(51) Int. Cl.
   *A61B 5/1455*      (2006.01)
   *A61B 5/00*      (2006.01)
   (Continued)

(52) U.S. Cl.
   CPC ........ *A61B 5/1455* (2013.01); *A61B 5/14532* (2013.01); *A61B 5/681* (2013.01);
     (Continued)

(58) Field of Classification Search
   CPC ... A61B 5/1455; A61B 5/14532; A61B 5/681; A61B 2562/0238; A61B 2562/046;
     (Continued)

(56) References Cited

U.S. PATENT DOCUMENTS 5,870,512 A *   2/1999   Koch ..................... H04B 10/54
                                       385/24
7,257,283 B1 *   8/2007   Liu ..................... G02B 6/12004
                                       385/24

(Continued)

FOREIGN PATENT DOCUMENTS

EP      3 002 568 A1    4/2016
JP      4475601 B2    6/2010

(Continued)

OTHER PUBLICATIONS

International Search Report and written opinion dated Sep. 13, 2024, issued in International Application No. PCT/KR2024/007875.

*Primary Examiner* — Sang H Nguyen

(74) *Attorney, Agent, or Firm* — Jefferson IP Law, LLP

(57) ABSTRACT

An electronic device is provided. The electronic device includes a transmission circuit, a reception circuit, memory storing one or more computer programs, and one or more processors communicatively coupled to the transmission circuit, the reception circuit, and the memory, wherein the transmission circuit includes a laser gain circuit configured to output or generate a plurality of laser lights in a broadband under control of the one or more processors, a fixed array distributed bragg reflector (DBR) grating configured to change wavelengths of the plurality of laser lights and output a plurality of laser lights having specified wavelengths, a modulator configured to modulate the plurality of laser lights having the specified wavelengths, a monitoring circuit configured to identify whether or not the plurality of (Continued)

modulated laser lights is output in a specified intensity and specified wavelength, and an output coupler configured to adjust output directions and/or angles of the plurality of modulated laser lights and output the plurality of modulated laser lights to an outside of the electronic device.

20 Claims, 20 Drawing Sheets

(51) Int. Cl.

| | |
|---|---|
| *A61B 5/145* | (2006.01) |
| *G04G 21/02* | (2010.01) |
| *H01S 5/00* | (2006.01) |
| *H01S 5/125* | (2006.01) |

(52) U.S. Cl.
CPC ......... *G04G 21/025* (2013.01); *H01S 5/0071* (2013.01); *H01S 5/125* (2013.01); *A61B 2562/0238* (2013.01); *A61B 2562/046* (2013.01)

(58) Field of Classification Search
CPC ..... G04G 21/025; H01S 5/0071; H01S 5/125; H01S 5/4087
See application file for complete search history.

(56) References Cited

U.S. PATENT DOCUMENTS

| 7,295,783 B2 | 11/2007 | Singh et al. | |
| 7,734,191 B1 * | 6/2010 | Welch ................ | H04B 10/2914 398/25 |
| 10,139,278 B2 | 11/2018 | Fish et al. | |

| 2008/0044128 A1 * | 2/2008 | Kish .................. | G02B 6/12033 385/14 |
|---|---|---|---|
| 2010/0056887 A1 | 3/2010 | Kimura et al. | |
| 2010/0166424 A1 * | 7/2010 | Nagarajan ............. | H01S 5/0265 398/79 |
| 2015/0303653 A1 * | 10/2015 | Tanaka ................. | G02B 6/1228 372/7 |
| 2015/0333475 A1 * | 11/2015 | Blumenthal .......... | H01S 5/0206 372/27 |
| 2016/0161685 A1 | 6/2016 | Xu et al. | |
| 2017/0095168 A1 * | 4/2017 | Kwon ................ | A61B 5/02125 |
| 2017/0254746 A1 | 9/2017 | Sugawa et al. | |
| 2018/0008175 A1 | 1/2018 | Ishizawa et al. | |
| 2019/0052056 A1 * | 2/2019 | Onaka .................... | G02B 6/105 |
| 2019/0246963 A1 * | 8/2019 | Chung .............. | A61B 5/14532 |
| 2020/0333312 A1 | 10/2020 | Islam | |
| 2021/0259565 A1 | 8/2021 | Ohno et al. | |
| 2022/0021458 A1 * | 1/2022 | Woodward ........... | H04B 10/613 |
| 2022/0052765 A1 * | 2/2022 | Torbatian ......... | H04B 10/07951 |
| 2022/0146766 A1 * | 5/2022 | Wang .................. | H04B 10/505 |
| 2022/0167855 A1 | 6/2022 | Kwon et al. | |
| 2023/0003938 A1 | 1/2023 | Zilkie et al. | |
| 2023/0074565 A1 | 3/2023 | Lee et al. | |
| 2023/0131237 A1 | 4/2023 | Park et al. | |

FOREIGN PATENT DOCUMENTS

| JP | 6344829 | B2 | 6/2018 |
|---|---|---|---|
| JP | 2020/099670 | A | 7/2020 |
| KR | 10-1296072 | B1 | 8/2013 |
| KR | 10-2017-0129705 | A | 11/2017 |
| KR | 10-2162833 | B1 | 10/2020 |
| KR | 10-2022-0076255 | A | 6/2022 |
| KR | 10-2022-0085321 | A | 6/2022 |
| KR | 10-2022-0127820 | A | 9/2022 |
| KR | 10-2498594 | B1 | 2/2023 |
| KR | 10-2023-0032697 | A | 3/2023 |

* cited by examiner

ELECTRONIC DEVICE AND METHOD FOR CONTROLLING SENSOR

CROSS-REFERENCE TO RELATED APPLICATION(S)

This application is a continuation application, claiming priority under § 365(c), of an International application No. PCT/KR2024/007875, filed on Jun. 10, 2024, which is based on and claims the benefit of a Korean patent application number 10-2023-0075486, filed on Jun. 13, 2023, in the Korean Intellectual Property Office, and of a Korean patent application number 10-2023-0093826, filed on Jul. 19, 2023, in the Korean Intellectual Property Office, the disclosure of each of which is incorporated by reference herein in its entirety.

TECHNICAL FIELD

The disclosure relates to an electronic device and a method for controlling a sensor.

BACKGROUND ART

Recently, electronic devices including sensors capable of measuring a user's biometric information and/or fitness data have been developed.

These electronic devices may generally be carried in a pocket or hand and used while moving, or they may also be configured to be worn on parts of the body or various structures. Electronic devices may provide health and fitness information by utilizing the fact that they are able to be worn on the user's body.

The above information is presented as background information only to assist with an understanding of the disclosure. No determination has been made, and no assertion is made, as to whether any of the above might be applicable as prior art with regard to the disclosure.

DISCLOSURE

Technical Problem

In order to detect blood sugar information among the user's biometric information, the electronic device may include a sensor capable of detecting blood sugar level non-invasively. However, non-invasive blood sugar detection sensors have difficulty in being mounted to mobile and/or wearable electronic devices due to the characteristics of a light source and a light reception element.

An electronic device and a sensor control method according to the disclosure aims to apply a miniaturized blood sugar detection sensor to a portable electronic device.

Aspects of the disclosure are to address at least the above-mentioned problems and/or disadvantages and to provide at least the advantages described below. Accordingly, an aspect of the disclosure is to provide to an electronic device and a method for controlling a sensor.

Additional aspects will be set forth in part in the description which follows and, in part, will be apparent from the description, or may be learned by practice of the presented embodiments.

Technical Solution

In accordance with an aspect of the disclosure, an electronic device is provided. The electronic device includes a transmission circuit, a reception circuit, memory storing one or more computer programs, and one or more processors communicatively coupled to the transmission circuit, the reception circuit, and the memory, wherein the transmission circuit includes a laser gain circuit configured to output or generate a plurality of laser lights in a broadband under control of the one or more processors, a fixed array distributed bragg reflector (DBR) grating configured to change wavelengths of the plurality of laser lights and output a plurality of laser lights having specified wavelengths, a modulator configured to modulate the plurality of laser lights having the specified wavelengths, a monitoring circuit configured to identify whether or not the plurality of modulated laser lights is output in a specified intensity and specified wavelength, and an output coupler configured to adjust output directions and/or angles of the plurality of modulated laser lights and output the plurality of modulated laser lights to an outside of the electronic device.

In an embodiment of the disclosure, the reception circuit may include at least one photo detector.

In an embodiment of the disclosure, the at least one photo detector may be spaced a specified distance apart from the output coupler.

In an embodiment of the disclosure, the laser gain circuit may include a plurality of laser gain chips and output or generate the plurality of laser lights in a broadband in time division.

In an embodiment of the disclosure, the specified wavelength may be shorter than the wavelengths of the plurality of laser lights.

In an embodiment of the disclosure, the modulator may modulate the plurality of laser lights having the specified wavelengths into continuous waves or pulse waves.

In an embodiment of the disclosure, the modulator may include a lock-in amplifier and/or a low pass filter.

In an embodiment of the disclosure, the monitoring circuit may include an edge illuminated photodiode, a Mach-Zehnder interferometer (MZI) sensor, a ring resonator, a line coupling, and/or a splitter.

In an embodiment of the disclosure, the monitoring circuit may be disposed between and connected to the output coupler and the modulator.

In an embodiment of the disclosure, the one or more processors may control time synchronization of the reception circuit to receive the plurality of modulated laser lights in time division and/or sequence.

In an embodiment of the disclosure, the reception circuit may include a plurality of photo detectors.

In an embodiment of the disclosure, each of the plurality of photo detectors may be spaced a first specified distance apart from the output coupler.

In an embodiment of the disclosure, each of the plurality of photo detectors of the reception circuit may be spaced a first specified distance or a second specified distance apart from the output coupler.

In an embodiment of the disclosure, the one or more processors may control the intensity and wavelength of light output from the laser gain circuit, based on information received from the monitoring circuit.

In an embodiment of the disclosure, the electronic device may include a case having the transmission circuit and the reception circuit disposed on the rear surface thereof, a display disposed on the front surface of the case, and a band connected to the case and configured to enable the electronic device to be worn on the user's wrist.

In an embodiment of the disclosure, the rear surface of the case is configured to at least partially come into contact with a user when the electronic device is worn on the user using the band.

In an embodiment of the disclosure, the rear surface of the case is configured such that at least a portion of the output coupler and at least a portion of the reception circuit are exposed.

In an embodiment of the disclosure, a method for controlling a sensor in an electronic device may include controlling a laser gain circuit to output or generate a plurality of laser lights in a broadband, performing control to change wavelengths of the laser lights in a broadband, based on a fixed array DBR grating, and output a plurality of laser lights having specified wavelengths, modulating the plurality of laser lights having the specified wavelengths, identifying whether or not the plurality of modulated laser lights is output in a specified intensity and specified wavelength, adjusting output directions and/or angles of the plurality of modulated laser lights and outputting the same to an outside of the electronic device, and detecting the plurality of modulated laser lights through a reception circuit.

In an embodiment of the disclosure, the sensor control method of the electronic device may include outputting or generating the plurality of laser lights in a broadband in time division.

In an embodiment of the disclosure, the sensor control method of the electronic device may include modulating the plurality of laser lights having the specified wavelengths into continuous waves or pulse waves.

In an embodiment of the disclosure, the sensor control method of the electronic device may include controlling time synchronization of the reception circuit to receive the plurality of modulated laser lights in time division and/or sequence.

In accordance with another aspect of the disclosure, an electronic device is provided. The electronic device includes a transmission circuit, a reception circuit, memory storing one or more computer programs, and one or more processors communicatively coupled to the transmission circuit, the reception circuit, and the memory, wherein the one or more computer programs include computer-executable instructions that, when executed by the one or more processors, cause the electronic device to control a laser gain circuit to output or generate a plurality of laser lights in a broadband, perform control to change wavelengths of the laser lights in a broadband, based on a fixed array DBR grating, and output a plurality of laser lights having specified wavelengths, modulate the plurality of laser lights having the specified wavelengths, identify whether or not the plurality of modulated laser lights is output in a specified intensity and specified wavelength, adjust output directions and/or angles of the plurality of modulated laser lights and outputting the same to an outside of the electronic device, and detect the plurality of modulated laser lights through a reception circuit.

In accordance with another aspect of the disclosure, one or more non-transitory computer-readable storage media storing one or more computer programs including computer-executable instructions that, when executed by one or more processors of an electronic device, cause the electronic device to perform operations are provided. The operations include controlling a laser gain circuit to output or generate a plurality of laser lights in a broadband, performing control to change wavelengths of the laser lights in a broadband, based on a fixed array DBR grating, and output a plurality of laser lights having specified wavelengths, modulating the plurality of laser lights having the specified wavelengths, identifying whether or not the plurality of modulated laser lights is output in a specified intensity and specified wavelength, adjusting output directions and/or angles of the plurality of modulated laser lights and outputting the same to an outside of the electronic device, and detecting the plurality of modulated laser lights through a reception circuit.

Advantageous Effects

The electronic device and sensor control method of the disclosure may improve the performance of the blood sugar detection sensor and miniaturize the same using a laser light source and/or a plurality of light reception elements, thereby easily detecting the user's biometric information.

Other aspects, advantages, and salient features of the disclosure will become apparent to those skilled in the art from the following detailed description, which, taken in conjunction with the annexed drawings, discloses various embodiments of the disclosure.

DESCRIPTION OF DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

MODE FOR INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and configurations may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

It should be appreciated that the blocks in each flowchart and combinations of the flowcharts may be performed by one or more computer programs which include instructions. The entirety of the one or more computer programs may be stored in a single memory device or the one or more computer programs may be divided with different portions stored in different multiple memory devices.

Any of the functions or operations described herein can be processed by one processor or a combination of processors. The one processor or the combination of processors is circuitry performing processing and includes circuitry like an application processor (AP, e.g. a central processing unit (CPU)), a communication processor (CP, e.g., a modem), a graphics processing unit (GPU), a neural processing unit (NPU) (e.g., an artificial intelligence (AI) chip), a Wi-Fi chip, a Bluetooth® chip, a global positioning system (GPS) chip, a near field communication (NFC) chip, connectivity chips, a sensor controller, a touch controller, a finger-print sensor controller, a display drive integrated circuit (IC), an audio CODEC chip, a universal serial bus (USB) controller, a camera controller, an image processing IC, a microprocessor unit (MPU), a system on chip (SoC), an integrated circuit (IC), or the like.

Figure 1:
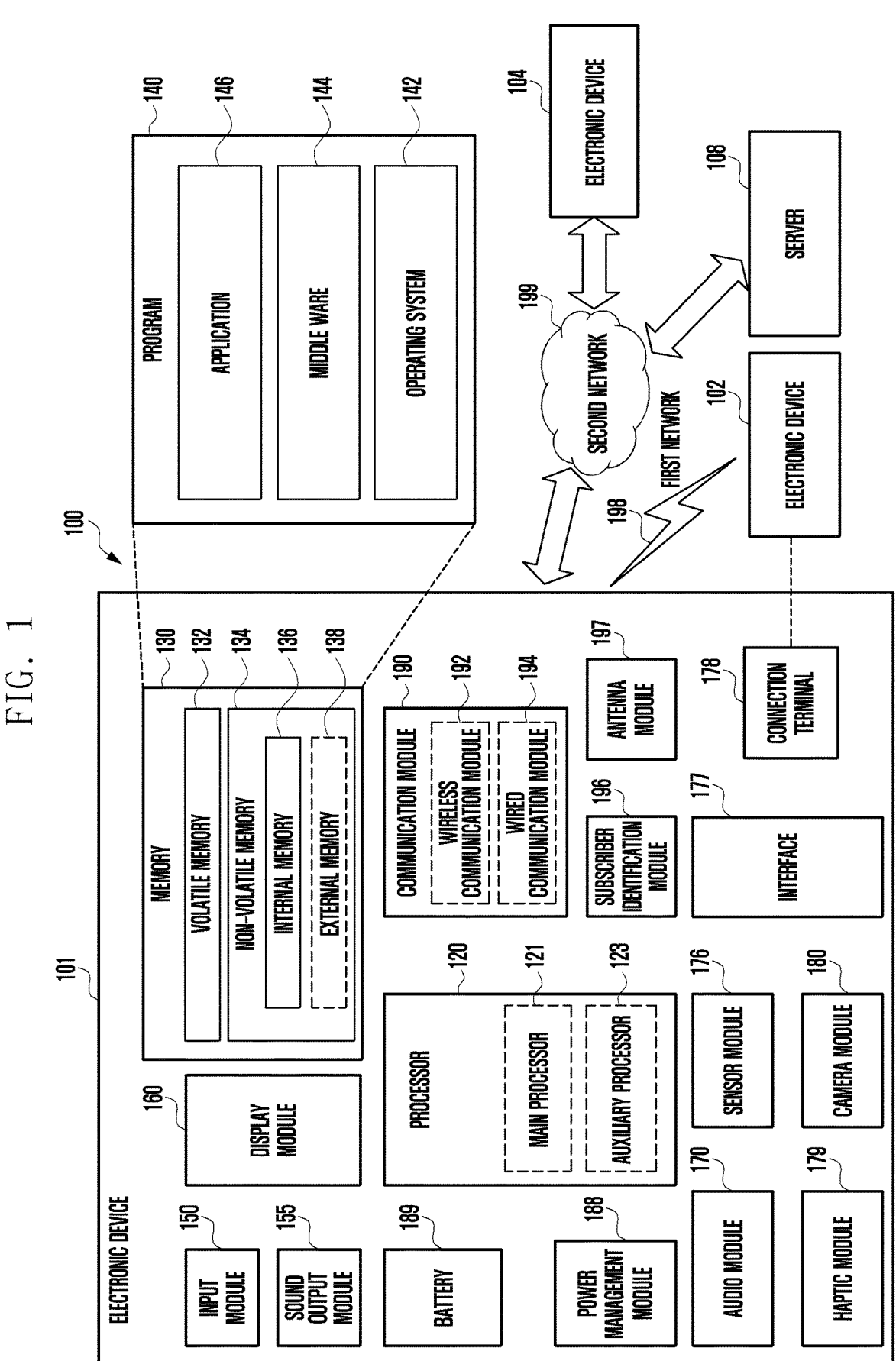
FIG. 1 is a block diagram of an electronic device in a network environment according to an embodiment of the disclosure.

FIG. 1 is a block diagram illustrating an electronic device 101 in a network environment 100 according to an embodiment of the disclosure.

Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). In an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may be configured to execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may be configured to store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, an HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a fifth generation (5G) network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a fourth generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the millimeter wave (mmWave) band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, an RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
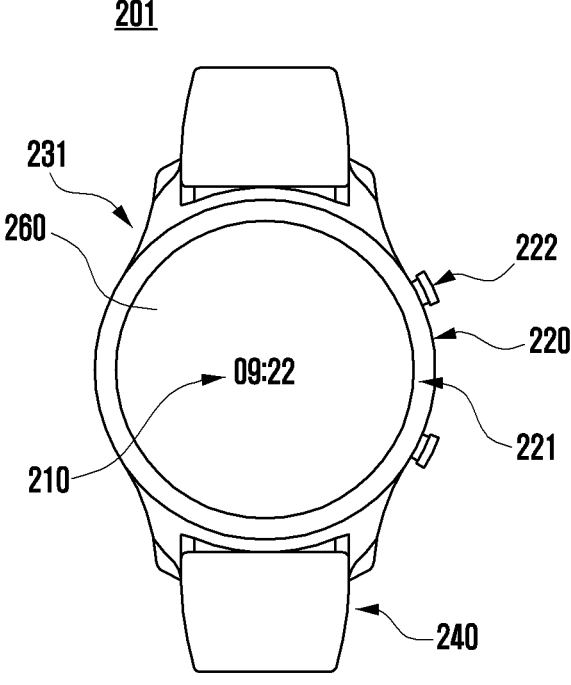
FIG. 2 is a diagram illustrating an electronic device according to an embodiment of the disclosure.

FIG. 2 is a diagram illustrating an electronic device 201 according to an embodiment of the disclosure.

In an embodiment, the elements of an electronic device 201 in FIG. 2 may be identical or similar to the elements of an electronic device 101 in FIG. 1. However, the disclosure is not limited thereto, and the electronic device 201 in FIG.

2 may further include other elements in addition to those of the electronic device 101 in FIG. 1, or may exclude some thereof.

In an embodiment, the electronic device 201 may include a display 260 (e.g., the display module 160 in FIG. 1) on the first surface or front surface 231. The electronic device 201 may be a watch-type wearable device to be worn on the user. The electronic device 201 may display a watch-related interface 210 on at least portion of the display 260.

In an embodiment, the electronic device 201 may include a case 220 and a band 240.

In an embodiment, the case 220 may include a bezel 221, a crown 222, and a display 260 on the outer side. The case 220, referring to FIG. 1, may include a processor 120, memory 130, an input module 150, a sound output module 155, a display module 160, an audio module 170, a sensor module 176, an interface 177, a connection terminal 178, a haptic module 179, a camera module 180, a power management module 188, a battery 189, a communication module 190, a subscriber identification module 196, and/or an antenna module 197 internally or externally.

In an embodiment, the display 260 may be disposed on the first surface 231 of the case 220, and at least a portion (e.g., the output coupler 315 and/or the photo detector in FIG. 3) of a sensor circuit (e.g., the sensor circuit 300 in FIG. 3) may be exposed to the outside through a second surface (e.g., the second surface 232 in FIGS. 8A to 8I).

In an embodiment, the second surface 232 of the case 220 may be at least partially in contact with the user when the electronic device 201 is worn on the user using the band 240.

In an embodiment, the bezel 221 may have a ring shape having the same center as the circular display 260. The inner radius of the bezel 221 may be the same as the radius of the display 260. The bezel 221 may be disposed at the edge of the case 220 to protect the display 260 from external impact.

In an embodiment, the bezel 221 may rotate in at least one of the clockwise direction or the counterclockwise direction. The bezel 221 may serve as an input device of the electronic device 201. If the bezel 221 rotates, the electronic device 201 may determine the rotation speed and rotation direction of the bezel 221 as an user input, and control the functions of the electronic device 201 according to the user input.

In an embodiment, the crown 222 may be disposed to protrude from at least a portion of the case 220. The crown 222 may have a cylindrical shape. The crown 222 may be connected to the case 220 to rotate around the rotation axis. The crown 222 may rotate while being connected to the case 220 through a stem that provides a rotation axis.

In an embodiment, the crown 222 may serve as an input device of the electronic device 201. If the crown 222 rotates, the electronic device 201 may determine the rotation speed and rotation direction of the crown 222 as an user input, and control the functions of the electronic device 201 according to the user input.

In an embodiment, the band 240 may enable the electronic device 201 to be worn on the user's wrist. The band 240 may be made of various materials such as metal, rubber, and leather. The band 240 may be connected to one end of the case 220, and the band 240 connected to the case 220 may be replaceable.

Figure 3:
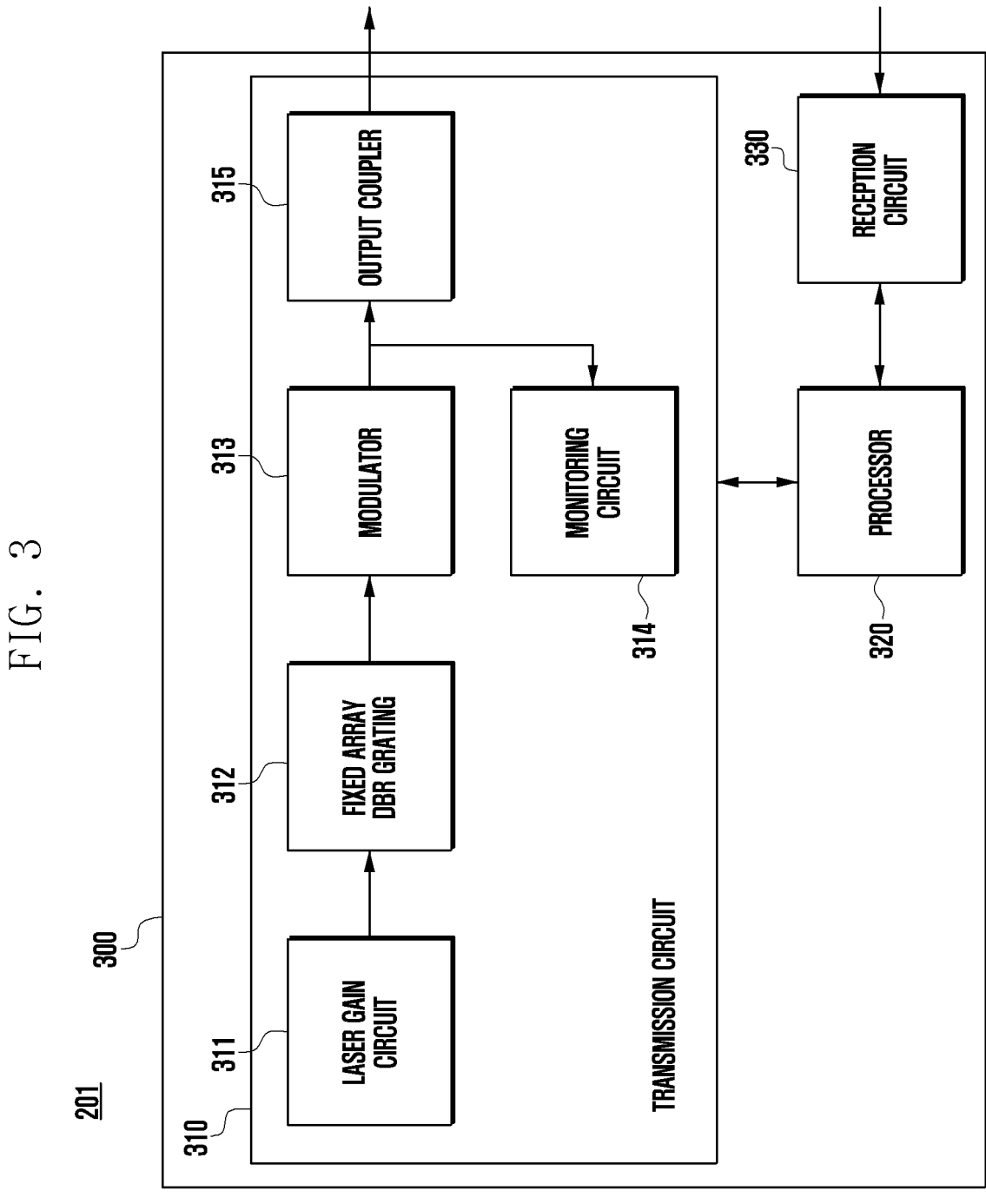
FIG. 3 is a block diagram illustrating a sensor circuit of an electronic device according to an embodiment of the disclosure.

FIG. 3 is a block diagram illustrating a sensor circuit 300 of an electronic device 201 according to an embodiment of the disclosure.

Figure 4:
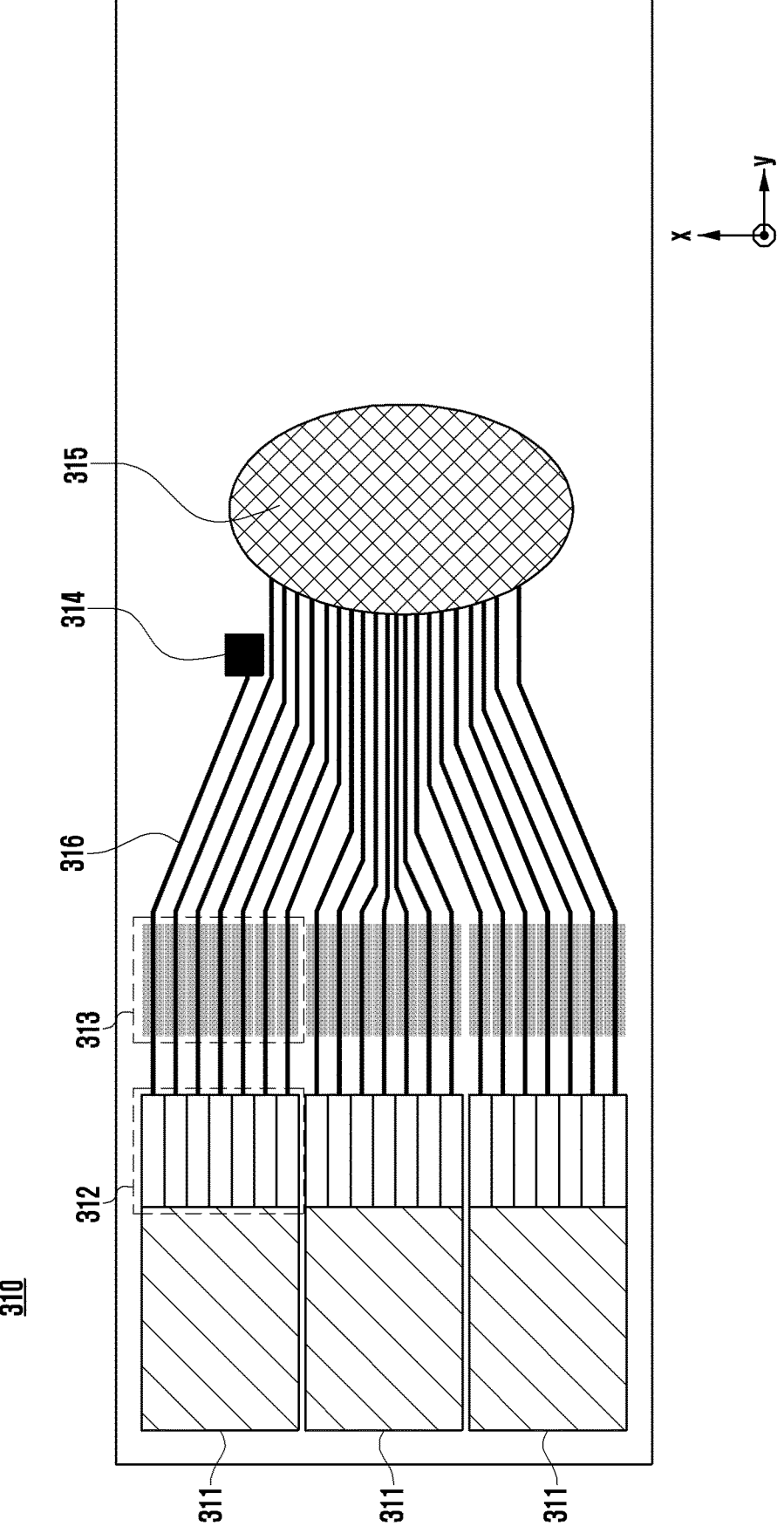
FIG. 4 is a diagram illustrating a transmission circuit implemented in a silicon-based integrated circuit according to an embodiment of the disclosure.

FIG. 4 is a diagram illustrating a transmission circuit 310 implemented in a silicon-based integrated circuit according to an embodiment of the disclosure.

Referring to FIGS. 3 and 4, a sensor circuit 300 in FIG. 3 may be the same as a sensor module 176 in FIG. 1 or may be included in the sensor module 176 in FIG. 1.

In an embodiment, the sensor circuit 300 may include a transmission circuit 310, a processor 320, and/or a reception circuit 330.

In an embodiment, the transmission circuit 310 may include a laser gain circuit 311, a fixed array distributed Bragg reflector (DBR) grating 312, a modulator 313, a monitoring circuit 314, and/or an output coupler 315.

In an embodiment, the laser gain circuit 311 may include a plurality of laser gain chips. However, the disclosure is not limited thereto, and the laser gain circuit 311 may include at least one laser gain chip.

In an embodiment, the laser gain circuit 311 may output and/or generate a broadband laser light under the control of the processor 320. The laser gain circuit 311 may output and/or generate a laser light with a wavelength ranging from about 2100 nm to about 2400 nm. A wavelength in the range of about 2100 nm to about 2400 nm of the laser light may be a wavelength appropriate for detecting blood sugar (or glucose).

In an embodiment, blood sugar may absorb at least some of the plurality of modulated laser lights output from the sensor circuit 300. The electronic device 201 may receive a plurality of modulated laser lights, at least some of which are absorbed into blood sugar, using a photo detector in the reception circuit 330, and identify the concentration of blood sugar according to the amount (or intensity) and/or wavelength of the received light under the control of the processor 320.

In an embodiment, the laser gain circuit 311 may output and/or generate a plurality of broadband laser lights under the control of the processor 320.

In an embodiment, the laser gain circuit 311 may output and/or generate a plurality of broadband laser lights in time division under the control of the processor 320.

In an embodiment, the plurality of laser gain chips may output and/or generate a broadband laser light in time division under the control of the processor 320.

In an embodiment, the processor 320 in FIG. 3 may be the same as processor 120 in FIG. 1. However, the disclosure is not limited thereto, and the processor 320 in FIG. 3 may be independent of the processor 120 in FIG. 1 and may be included in the sensor circuit 300. The processor 320 may be implemented in the form of an application-specific integrated circuit (ASIC).

In an embodiment, the fixed array DBR grating 312 may change the wavelength of the broadband laser light output and/or generated from the laser gain circuit 311 to output a laser light with a specified wavelength. The specified wavelength may be shorter than the wavelength output from the laser gain circuit 311.

In an embodiment, the fixed array DBR grating 312 may change the wavelengths of the broadband laser lights output and/or generated from the plurality of laser gain circuits 311 and output a plurality of laser lights with specified wavelengths.

In an embodiment, the fixed array DBR grating 312 may correspond to each laser gain chip and change the wavelength of the broadband laser output and/or generated by each laser gain chip to output a plurality of laser lights with specified wavelengths.

In an embodiment, the modulator 313 may modulate a plurality of laser lights with specified wavelengths output from the fixed array DBR grating 312 under the control of the processor 320. In order to improve the signal-to-noise ratio of the output laser light, the sensor circuit 310 may modulate a plurality of laser lights with specified wavelengths output from the fixed array DBR grating 312 using the modulator 313.

In an embodiment, the modulator 313 may modulate a laser light having a specified wavelength into a continuous wave and/or a pulse wave.

In an embodiment, modulator 313 may include a lock-in amplifier and/or a low pass filter.

In an embodiment, the modulator 313 may modulate a plurality of laser lights with specified wavelengths output from the fixed array DBR grating 312 to output a plurality of modulated laser lights.

In an embodiment, the plurality of modulated laser lights output from the modulator 313 may be transmitted to the output coupler 315 through a waveguide (e.g., the waveguide 316 in FIG. 4).

In an embodiment, the output coupler 315 may change the output directions of the plurality of modulated laser lights and output the same to the outside of the transmission circuit 310. For example, referring to FIG. 4, if the light moves on the x-y coordinate plane in the transmission circuit 310 implemented in a silicon-based integrated circuit reaches the output coupler 315, it may be output in the z-axis, which is the vertical direction of the coordinate plane.

In an embodiment, the output coupler 315 may adjust the output directions and/or angles of the modulated laser lights under the control of the processor 320 to output the same to the outside of the transmission circuit 310.

In an embodiment, the monitoring circuit 314 may include an edge-illuminated photodiode, a Mach-Zehnder interferometer (MZI) sensor, a ring resonator, a line coupling, and/or a splitter.

In an embodiment, the monitoring circuit 314 may identify and/or monitor whether or not a plurality of modulated laser lights transmitted through a waveguide (e.g., the waveguide 316 in FIG. 4) is output in a specified intensity (or power) and a specified wavelength.

In an embodiment, the monitoring circuit 314 may identify at least some of the modulated laser lights transmitted through a waveguide (e.g., the waveguide 316 in FIG. 4).

For example, if the light output from the transmission circuit 310 falls outside of the specified intensity and wavelength, the concentration of blood sugar detected may be measured inaccurately by the processor 320 and/or the electronic device 201. The monitoring circuit 314 may identify whether the plurality of modulated laser lights transmitted through a waveguide (e.g., the waveguide 316 in FIG. 4) is output in a specified intensity (or power) and a specified wavelength, and transmit the identified information to the processor 320. The processor 320 may control the intensity and wavelength of light output from the laser gain circuit 311, based on the information received through the monitoring circuit 314. The information may include data on whether a plurality of modulated laser lights is output in a specified intensity (or power) and a specified wavelength.

In an embodiment, an edge illuminated photodiode of the monitoring circuit 314 may detect the intensity of light reaching the monitoring circuit 314. The Mach-Zehnder interferometer sensor of the monitoring circuit 314 may detect the wavelength of light reaching the monitoring circuit 314.

In an embodiment, the monitoring circuit 314 may be disposed between and connected to the modulator 313 and the output coupler 315. However, the disclosure is not limited thereto, and the monitoring circuit 314 may be disposed between and connected to the fixed array DBR grating 312 and the modulator 313.

In an embodiment, the reception circuit 330 may include a photo detector. The reception circuit 330 may include a plurality of photo detectors. The reception circuit 330 may include at least one photo detector. The photo detector may be spaced a specified distance apart from a structure through which light is output from the transmission circuit 310. The structure through which light is output from the transmission circuit 310 may be, for example, an output coupler 315. However, the disclosure is not limited thereto, and the structure through which light is output from the transmission circuit 310 may include a light output structure and/or an opening corresponding to the output coupler 315. The photo detector may detect wavelengths in a band of about 2100 nm to about 2400 nm.

In an embodiment, there may be at least one distance by which the photo detector is spaced apart from the structure (e.g., the output coupler 315) through which light is output from the transmission circuit 310. There may be a plurality of distances by which the photo detector is spaced apart from the structure (e.g., the output coupler 315) through which light is output from the transmission circuit 310. For example, there may be a plurality of specified distances between a plurality of photo detectors and the structure (e.g., the output coupler 315) through which light is output from the transmission circuit 310, including a second distance or a third distance, as well as a first distance.

In an embodiment, the reception circuit 330 may receive light output from the transmission circuit 310. The reception circuit 330 may sequentially receive light output from the transmission circuit 310. The transmission circuit 310 may irradiate the user's skin in time division and/or sequence with a plurality of modulated laser lights having specified wavelengths. The light radiated on the user's skin in time division and/or sequence may pass through the user's skin to be received in sequence and/or time division by the reception circuit 330. The disclosure is not limited thereto, and the light radiated on the user's skin in time division and/or sequence may be reflected on the user's skin and then received in sequence and/or time division by the reception circuit 330.

According to an embodiment, the processor 320 may control the transmission circuit 310 and/or the reception circuit 330. The processor 320 may control a plurality of laser gain chips included in the laser gain circuit 311 to output a broadband laser light in time division. The processor 320 may control the transmission circuit 310 to output a plurality of modulated laser lights in time division. The processor 320 may control time synchronization of the reception circuit 330 to receive the plurality of modulated laser lights in time division and/or sequence. The processor 320 may demodulate the plurality of modulated laser lights received through the reception circuit 330. The processor 320 may include an amplifier and/or a filter to demodulate the plurality of modulated laser lights received through the reception circuit 330. However, the disclosure is not limited thereto, and the reception circuit 330 may include an amplifier and/or a filter to demodulate the plurality of modulated laser lights. The processor 320 may convert photocurrent into a digital signal. The processor 320 may include an analog-to-digital converter (ADC) that converts photocurrent into a digital signal. However, the disclosure is not limited thereto, and the reception circuit 330 may include an ADC that converts photocurrent into a digital signal. The processor 320 may include memory (e.g., the memory 130 in FIG. 1) and/or an interface for communication with the processor 120 in FIG. 1.

Figure 5:
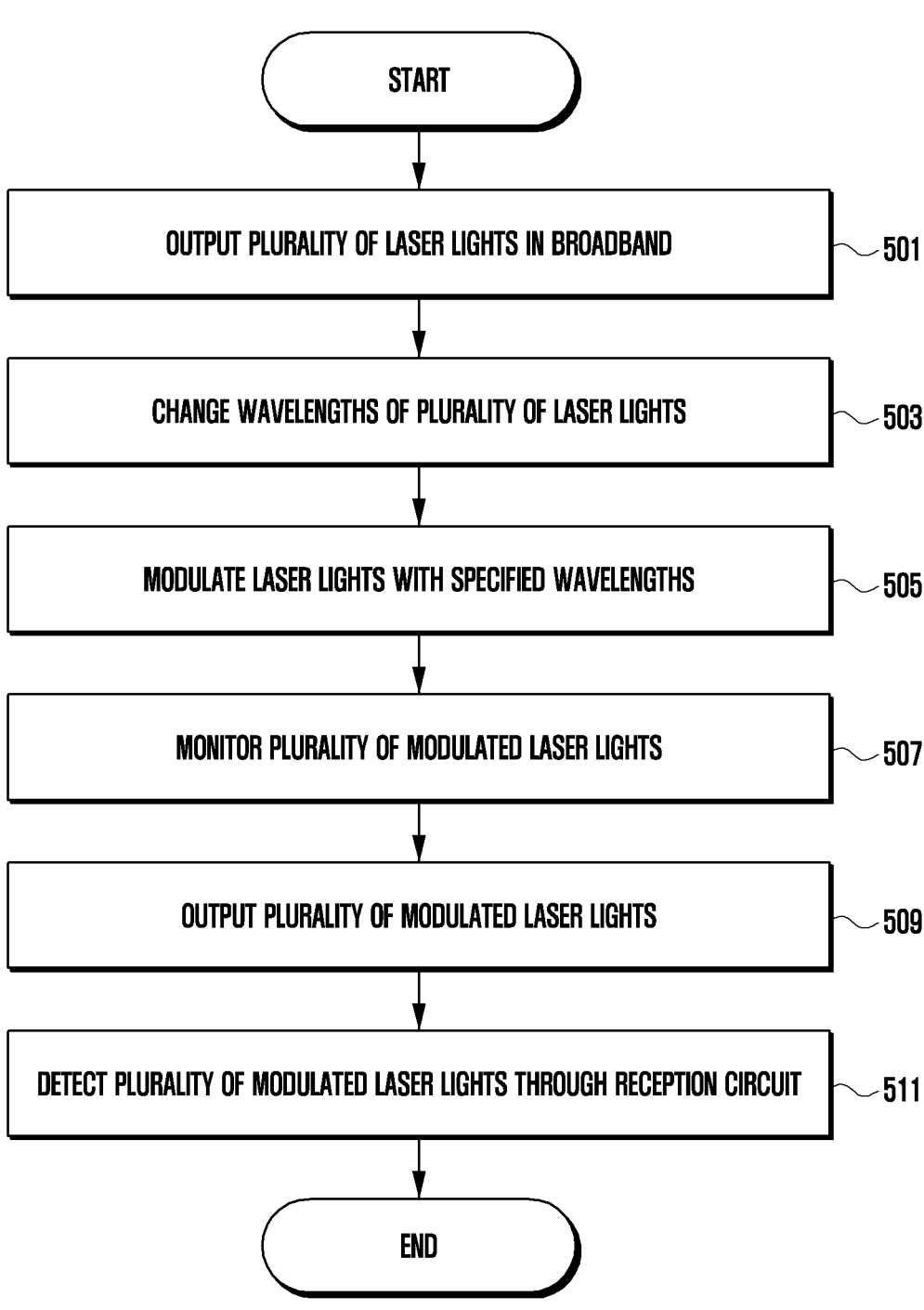
FIG. 5 is a flowchart illustrating a method for controlling a sensor circuit of an electronic device according to an embodiment of the disclosure.

FIG. 5 is a flowchart illustrating a method for controlling a sensor circuit 300 of an electronic device 201 according to an embodiment of the disclosure.

In the following embodiments, respective operations may be performed in sequence, but are not necessarily performed in sequence. For example, the sequence of the operations may vary, and at least two operations may be performed in parallel.

According to an embodiment, operations 501 to 511 may be understood as being performed by a processor (e.g., the processor 320 in FIG. 3) of an electronic device (e.g., the electronic device 201 in FIG. 3).

In an embodiment, the electronic device 201 may control the laser gain circuit 311 to output and/or generate a plurality of laser lights in a broadband under the control of the processor 320 in operation 501.

In an embodiment, in operation 501, the electronic device 201 may control a laser gain circuit (e.g., the laser gain circuit 311 in FIG. 3) to output and/or generate a plurality of broadband laser lights in time division under the control of the processor 320.

In an embodiment, in operation 503, the electronic device 201, under the control of the processor 320, may change the wavelengths of the broadband laser lights, based on a fixed array DBR grating (e.g., the fixed array DBR grating 312 in FIG. 3), thereby outputting a plurality of laser lights with specified wavelengths. The specified wavelength may be shorter than the wavelength output from the laser gain circuit 311.

In an embodiment, the electronic device 201, under the control of the processor 320, may modulate the plurality of laser lights with specified wavelengths output from the fixed array DBR grating 312 in operation 505. The electronic device 201 may modulate the laser light having a specified wavelength into a continuous wave and/or pulse wave.

In an embodiment, in operation 505, the electronic device 201, under the control of the processor 320, may modulate the plurality of laser lights with specified wavelengths output from the fixed array DBR grating 312, based on a modulator (e.g., the modulator 313 in FIG. 3). A sensor circuit (e.g., the sensor circuit 300 in FIG. 3) may modulate a laser light having a specified wavelength into a continuous wave and/or pulse wave.

In an embodiment, the electronic device 201 may monitor the plurality of modulated laser lights under the control of the processor 320 in operation 507.

In an embodiment, the electronic device 201, in operation 507, under the control of the processor 320, may identify and/or monitor whether or not the plurality of modulated laser lights is output in a specified intensity (or power) and specified wavelength, based on a monitoring circuit (e.g., the monitoring circuit 314 in FIG. 3).

In an embodiment, in operation 509, the electronic device 201, under the control of the processor 320, may adjust the output directions and/or angles of the modulated laser lights and output the same to the outside of a transmission circuit (e.g., the transmission circuit 310) or electronic device 201.

In an embodiment, in operation 509, the electronic device 201, under the control of the processor 320, may adjust the output directions and/or angles of the modulated laser lights, based on an output coupler (e.g., the output coupler 315 in FIG. 3), and output the same to the outside of the transmission circuit 310.

In an embodiment, in operation 511, the electronic device 201, under the control of the processor 320, may detect the plurality of modulated laser lights through a reception circuit (e.g., the reception circuit 330 in FIG. 3). The processor 320 may control time synchronization of the reception circuit 330 to receive the plurality of modulated laser lights in time division and/or sequence. The modulated laser lights may be light that is radiated onto an object and returns. The processor 320 may demodulate the plurality of modulated laser lights received through the reception circuit 330. The reception circuit 330 may be spaced a specified distance apart from a light output structure included in the output coupler 315. The light output structure may include a shape (e.g., an opening) through which a plurality of modulated laser lights is output.

In an embodiment, blood sugar may absorb at least some of the plurality of modulated laser lights output from the sensor circuit 300. The electronic device 201 may receive a plurality of modulated laser lights, some of which are absorbed into blood sugar, using a photo detector of the reception circuit 330 and, under the control of the processor 320, identify the concentration of blood sugar according to the amount (or intensity) and/or wavelength of the received light.

In an embodiment, blood sugar may reflect at least some of the plurality of modulated laser lights output from the sensor circuit 300. The electronic device 201 may receive a plurality of modulated laser lights, at least some of which are reflected from blood sugar, using the photo detector of the reception circuit 330 and, under the control of the processor 320, identify the concentration of blood sugar according to the amount (or intensity) and/or wavelength of the received light.

Figure 6A:
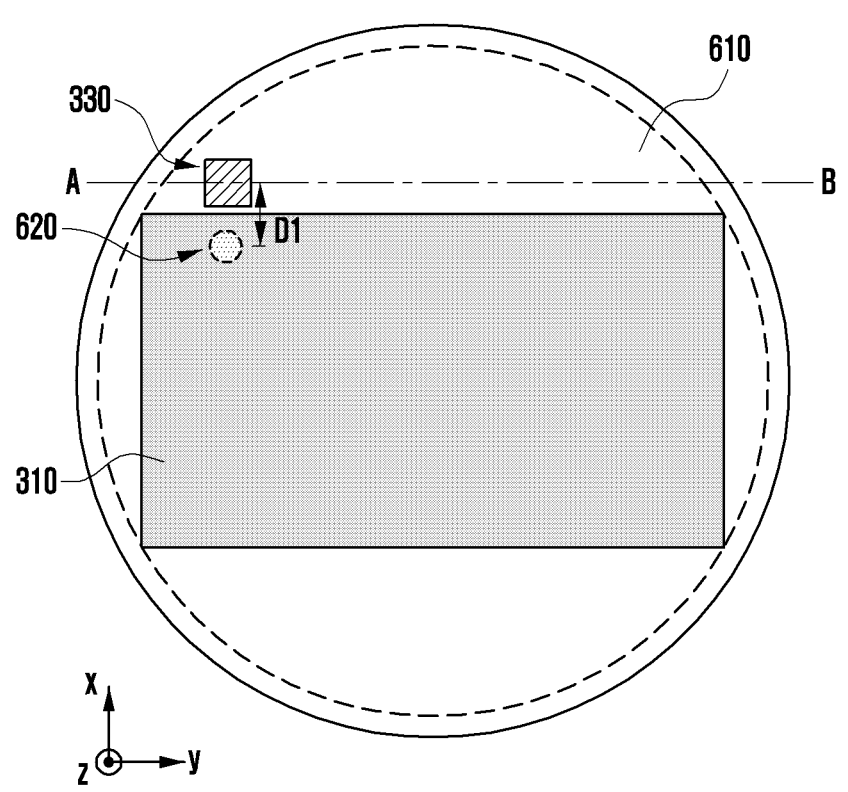
FIG. 6A is a diagram illustrating a transmission circuit and a reception circuit included in a substrate according to an embodiment of the disclosure.

FIG. 6A is a diagram illustrating a transmission circuit 310 and a reception circuit 330 included in a substrate 610 according to an embodiment of the disclosure.

Figure 6B:
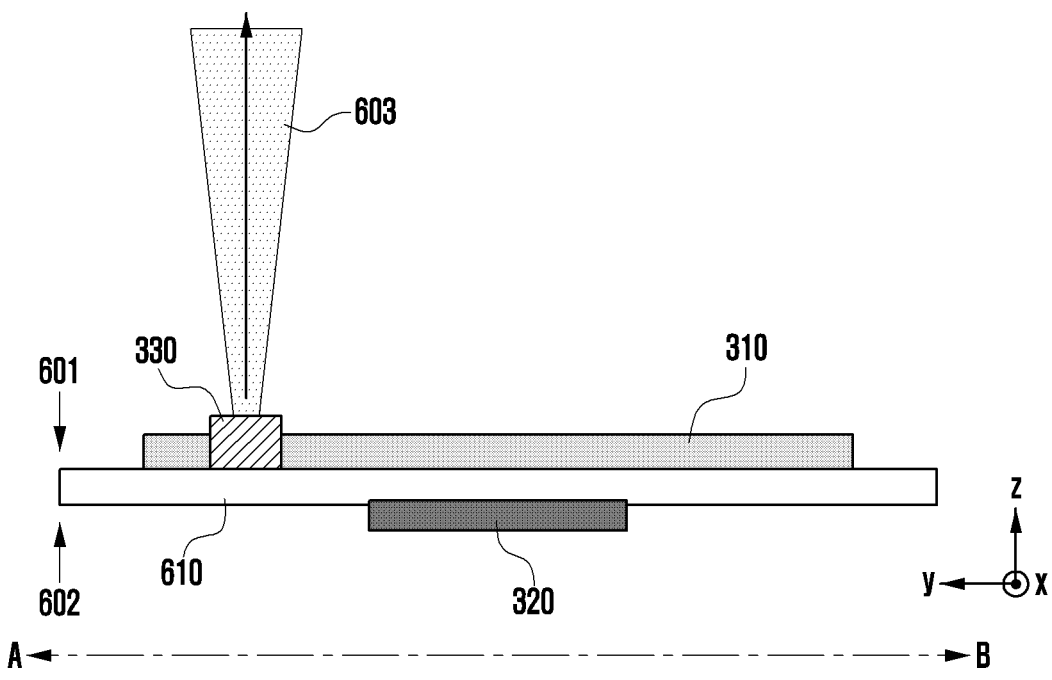
FIG. 6B is a cross-sectional view of the substrate in FIG. 6A taken along line A-B according to an embodiment of the disclosure.

FIG. 6B is a cross-sectional view of the substrate 610 in FIG. 6A taken along line A-B according to an embodiment of the disclosure.

Referring to FIGS. 6A and 6B, a substrate 610 may be processed into a shape similar to a case (e.g., a case 220 in FIG. 2) of an electronic device 201 so as to be coupled to the electronic device 201.

Referring to FIGS. 6A and 6B, the transmission circuit 310 and the reception circuit 330 may be disposed on a third surface 601 of the substrate 610, and the processor 320 may be disposed on a fourth surface 602 of the substrate 610.

In an embodiment, the third surface 601 of the substrate 610 may face the second surface or the rear surface (e.g., the rear surface 232 in FIGS. 8A to 8I) of the electronic device 201. The fourth surface 602 of the substrate 610 may face the first surface or the front surface (e.g., the front surface 231 in FIG. 2) of the electronic device 201.

In an embodiment, at least a portion of the transmission circuit 310 may include a light output structure 620 that outputs a plurality of modulated laser lights 603. The light output structure 620 may include an output coupler (e.g., the output coupler 315 in FIG. 3) in at least a part thereof. The light output structure 620 may correspond at least in part to the output coupler 315. The light output structure 620 and the reception circuit 330 may be spaced a specified distance D1 apart from each other. The transmission circuit 310 and the reception circuit 330 may be disposed on the substrate 610.

Figure 7A:
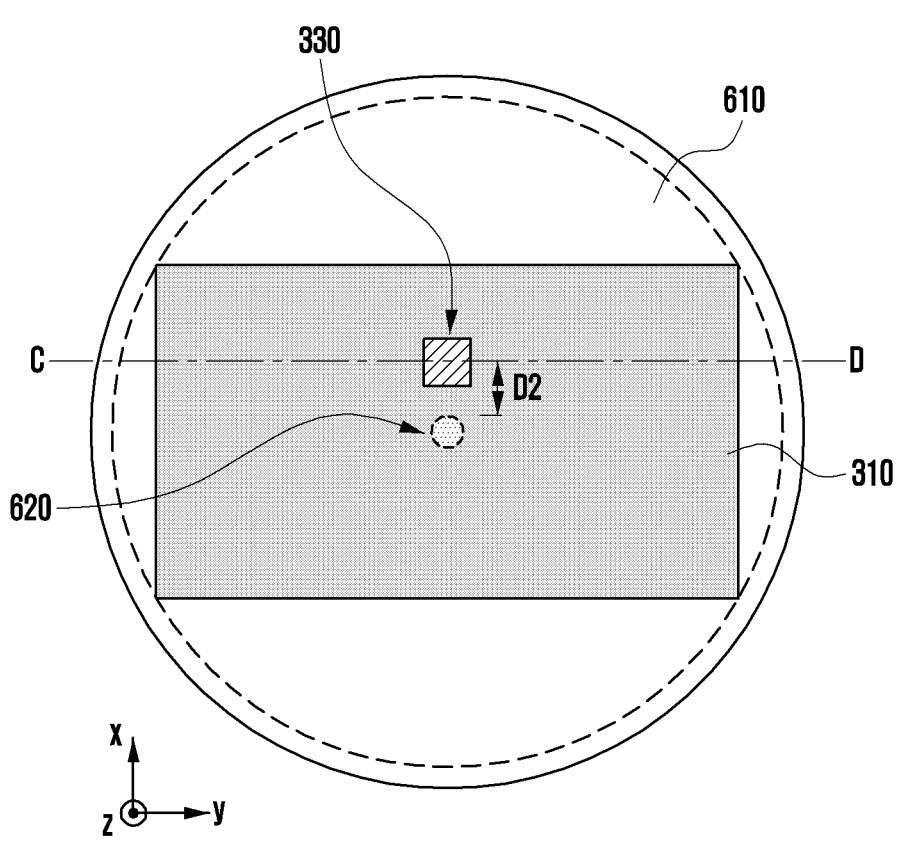
FIG. 7A is a diagram illustrating a transmission circuit and a reception circuit included in a substrate according to an embodiment of the disclosure.

FIG. 7A is a diagram illustrating a transmission circuit 310 and a reception circuit 330 included in a substrate 610 according to an embodiment of the disclosure.

Figure 7B:
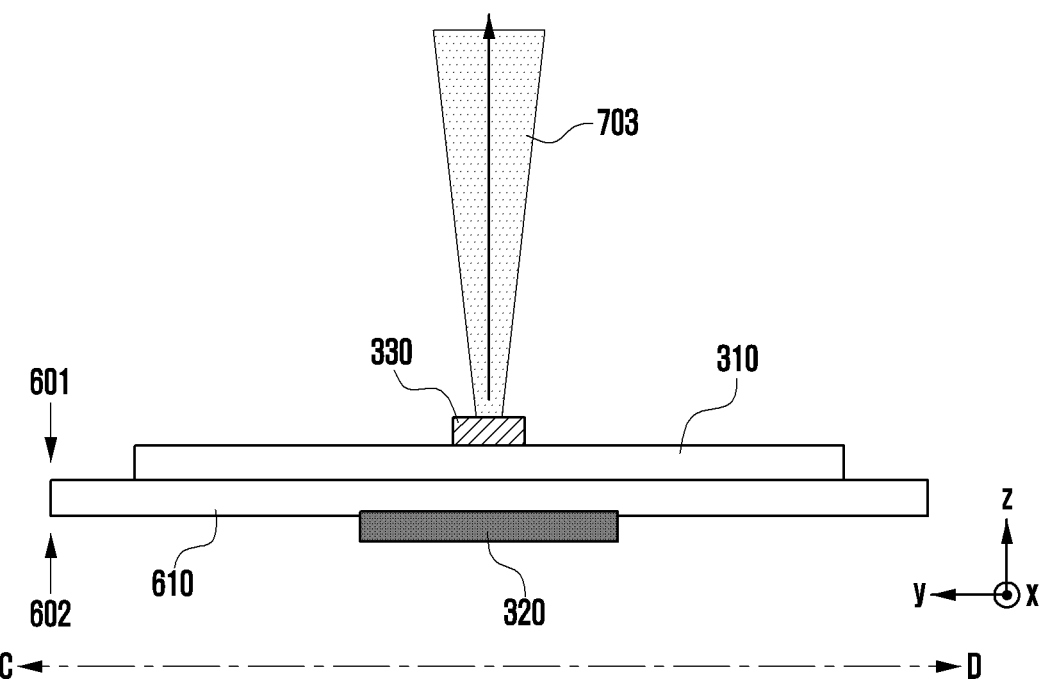
FIG. 7B is a cross-sectional view of the substrate in FIG. 7A taken along line C-D according to an embodiment of the disclosure.

FIG. 7B is a cross-sectional view of the substrate 610 in FIG. 7A taken along line C-D according to an embodiment of the disclosure.

Referring to FIGS. 7A and 7B, a substrate 610 may be processed into a shape similar to a case (e.g., a case 220 in FIG. 2) of an electronic device 201 so as to be coupled to the electronic device 201.

Referring to FIGS. 7A and 7B, the transmission circuit 310 may be disposed on a third surface 601 of the substrate 610, and the processor 320 may be disposed on a fourth surface 602 of the substrate 610. The reception circuit 330 may be disposed on the transmission circuit 310.

In an embodiment, the third surface 601 of the substrate 610 may face the second surface or the rear surface (e.g., the rear surface 232 in FIGS. 8A to 8I) of the electronic device 201. The fourth surface 602 of the substrate 610 may face the first surface or the front surface (e.g., the front surface 231 in FIG. 2) of the electronic device 201.

In an embodiment, at least a portion of the transmission circuit 310 may include a light output structure 620 that outputs a plurality of modulated laser lights 703. The light output structure 620 may include an output coupler (e.g., the output coupler 315 in FIG. 3) in at least a part thereof. The light output structure 620 may correspond at least in part to the output coupler 315.

In an embodiment, the light output structure 620 and the reception circuit 330 may be spaced a specified distance D2 apart from each other. The reception circuit 330 may be disposed on the transmission circuit 310. For example, the transmission circuit 310 may include the reception circuit 330 in at least apart thereof. The reception circuit 330 in FIGS. 7A and 7B may be disposed on the transmission circuit 310, and the transmission circuit 310 and the reception circuit 330 in FIGS. 6A and 6B may be disposed on the substrate 610.

The reception circuit 330 in FIGS. 7A and 7B may be disposed on the transmission circuit 310, and the transmission circuit 310 and reception circuit 330 in FIGS. 6A and 6B may be disposed on the substrate 610.

Figure 7C:
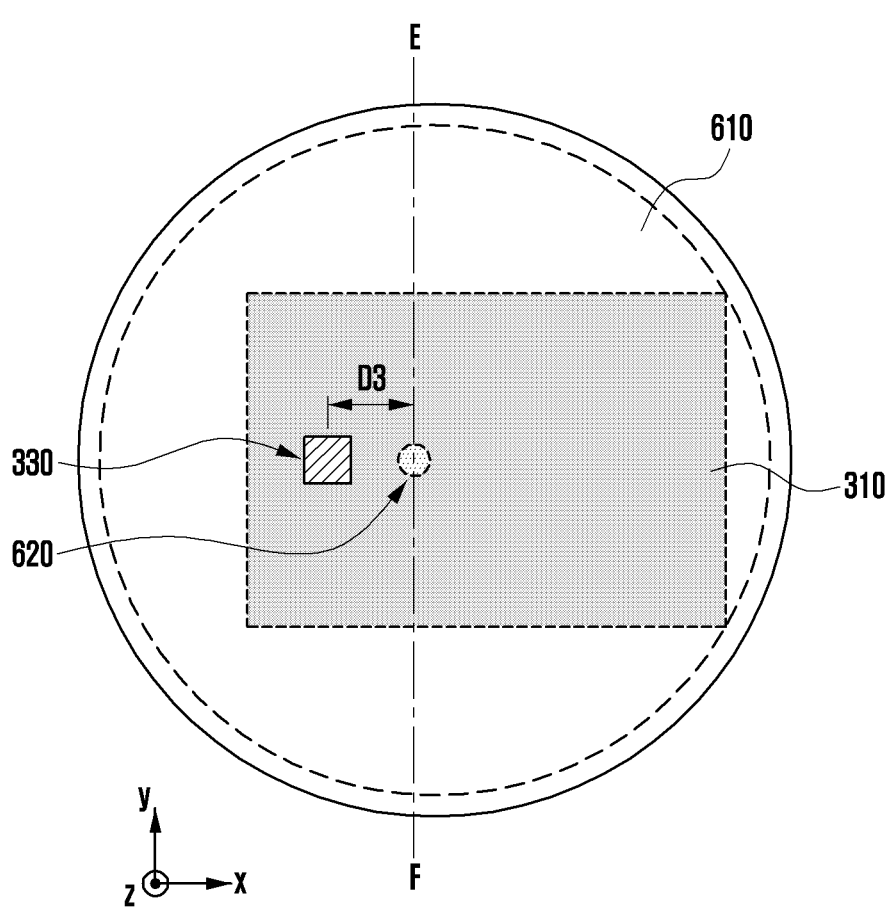
FIG. 7C is a diagram illustrating a transmission circuit and a reception circuit included in a substrate according to an embodiment of the disclosure.

FIG. 7C is a diagram illustrating a transmission circuit 310 and a reception circuit 330 included in a substrate 610 according to an embodiment of the disclosure.

Figure 7D:
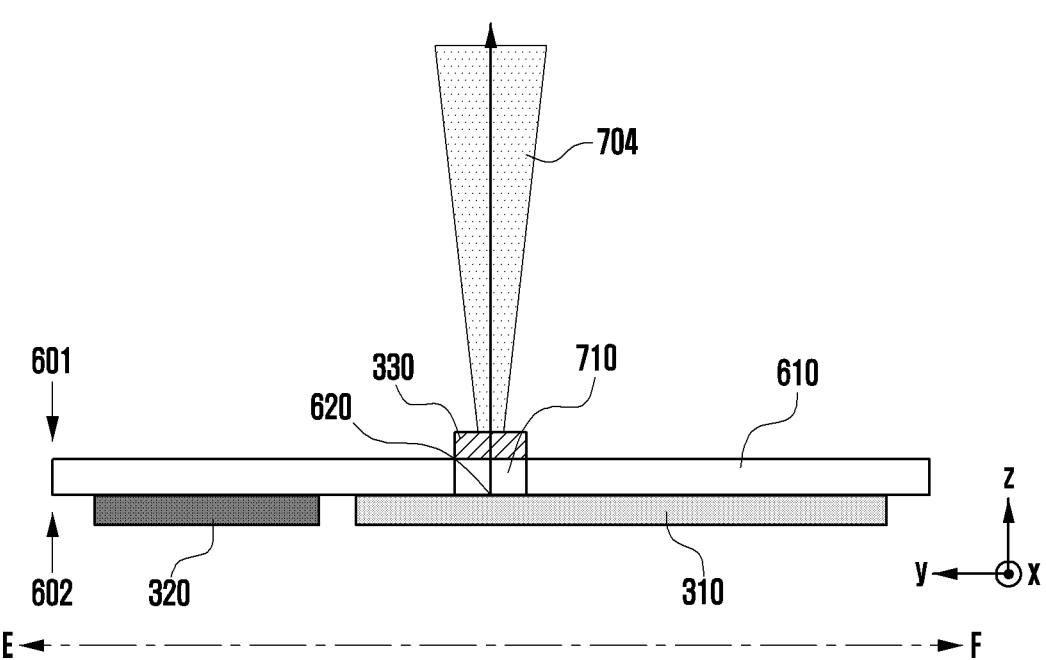
FIG. 7D is a cross-sectional view of the substrate in FIG. 7C taken along line E-F according to an embodiment of the disclosure.

FIG. 7D is a cross-sectional view of the substrate 610 in FIG. 7C taken along line E-F according to an embodiment of the disclosure.

Referring to FIGS. 7C and 7D, a substrate 610 may be processed into a shape similar to a case 220 of an electronic device 201 so as to be coupled to the electronic device 201.

Referring to FIGS. 7C and 7D, the reception circuit 330 may be disposed on a third surface 601 of the substrate 610, and the transmission circuit 310 and processor 320 may be disposed on fourth surface 602 of the substrate 610. The third surface 601 of the substrate 610 may face the second surface or the rear surface 232 of the electronic device 201. The fourth surface 602 of the substrate 610 may face the first surface or the front surface 231 of the electronic device 201.

In an embodiment, at least a portion of the transmission circuit 310 may include a light output structure 620 that outputs a plurality of modulated laser lights 704. The light output structure 620 may include the output coupler 315 in at least a part thereof. The light output structure 620 may correspond at least in part to the output coupler 315.

In an embodiment, the substrate 610 may include an opening 710 corresponding to the light output structure 620. The transmission circuit 310 disposed on the fourth surface 602 of the substrate 610 may output a plurality of modulated laser lights through the opening 710.

In an embodiment, the light output structure 620 and the reception circuit 330 may be spaced a specified distance D apart from each other.

Figure 8A:
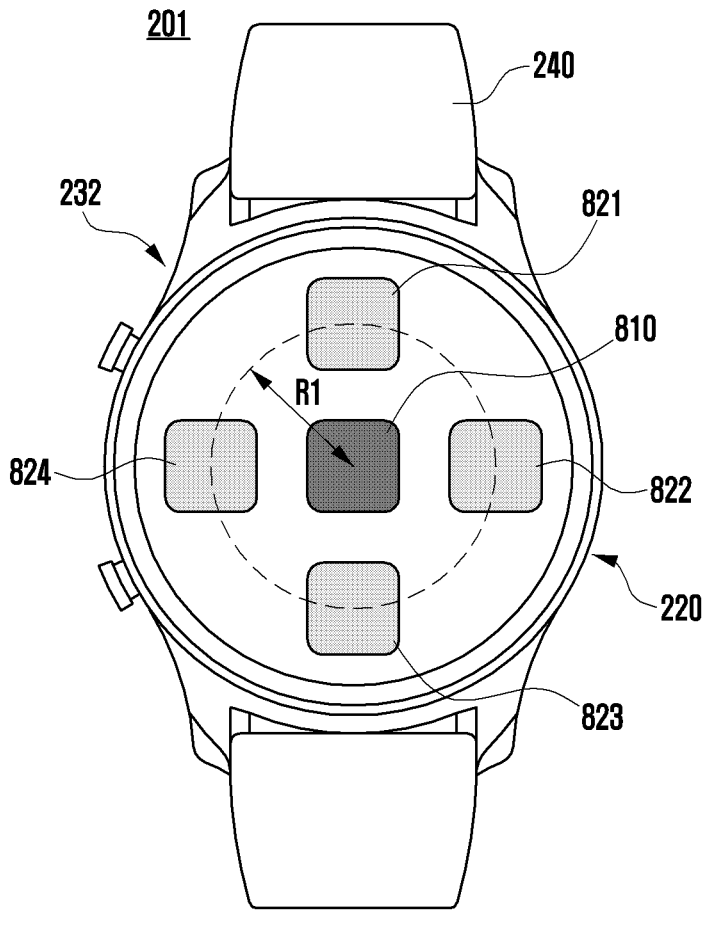
FIG. 8A is a diagram illustrating a light output structure and a light reception structure disposed on a second surface or rear surface of an electronic device according to an embodiment of the disclosure.

FIG. 8A is a diagram illustrating a sensor circuit 300 disposed on the second surface or the rear surface 232 of the electronic device 201 according to an embodiment of the disclosure.

In an embodiment, an electronic device 201 may include a light output structure 810 and a plurality of light reception structures 821, 822, 823, and 824 on a second surface 232. The light output structure 810 may include an output coupler (e.g., an output coupler 315 in FIG. 3) in at least a part thereof. The electronic device 201 may include the plurality of light reception structures 821, 822, 823, and 824 spaced a first distance R1 apart from the light output structure 810 at the center. The first distance R1 may have a specified length. Each of the plurality of light reception structures 821, 822, 823, and 824 may include a reception circuit 330 and/or a photo detector.

Referring to FIG. 8A, the first light reception structure 821, the second light reception structure 822, the third light reception structure 823, and the fourth light reception structure 824 may be disposed in the shape of a cross, based on the light output structure 810. The first light reception structure 821, the second light reception structure 822, the third light reception structure 823, and the fourth light reception structure 824 may have a rectangular shape having substantially the same size.

Figure 8B:
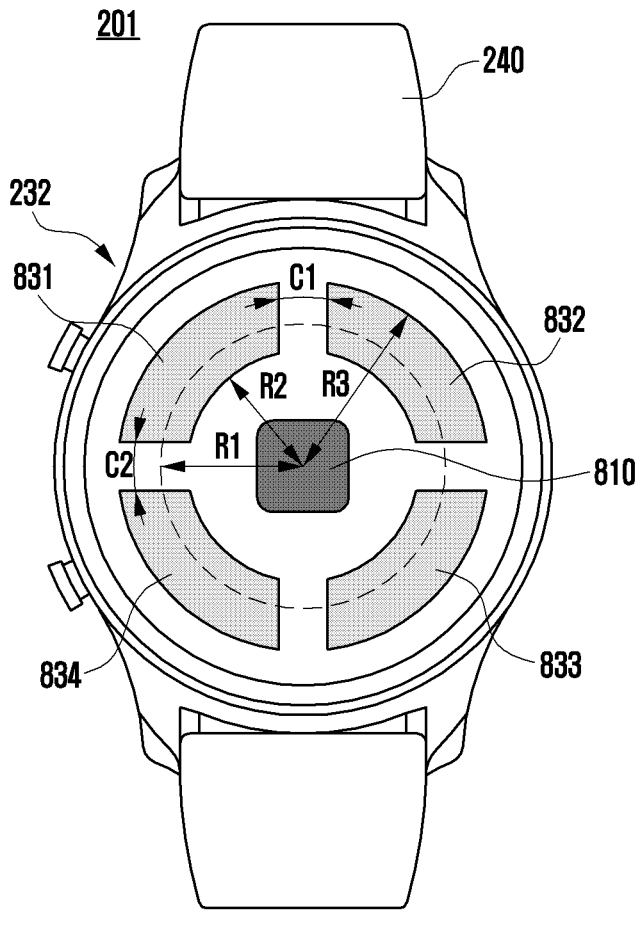
FIG. 8B is a diagram illustrating a light output structure and a light reception structure disposed on a second surface or rear surface of an electronic device according to an embodiment of the disclosure.

FIG. 8B is a diagram illustrating a light output structure and a light reception structure disposed on the second surface or the rear surface 232 of the electronic device 201 according to an embodiment of the disclosure.

In an embodiment, the electronic device 201 may include a light output structure 810 and a plurality of light reception structures 831, 832, 833, and 834 on the second surface 232. The light output structure 810 may include the output coupler 315 in at least a part thereof. The electronic device 201 may include a plurality of light reception structures 831, 832, 833, and 834 spaced a first distance R1 apart from the light output structure 810 at the center. The first distance R1 may have a specified length. Each of the plurality of light reception structures 831, 832, 833, and 834 may include a reception circuit 330 and/or a photo detector.

Referring to FIG. 8B, the fifth light reception structure 831, the sixth light reception structure 832, the seventh light reception structure 833, and the eighth light reception structure 834 may be disposed around the light output structure 810 as the center.

In an embodiment, the fifth light reception structure 831 may be spaced apart from the sixth light reception structure 832 by a first width C1 and spaced apart from the eighth light reception structure 834 by a second width C2. The sixth light reception structure 832 may be spaced apart from the fifth light reception structure 831 by the first width C1 and spaced apart from the seventh light reception structure 833 by the second width C2. The seventh light reception structure 833 may be spaced apart from the sixth light reception structure 832 by the second width C2 and spaced apart from the eighth light reception structure 834 by the first width C2. The eighth light reception structure 834 may be spaced apart from the seventh light reception structure 833 by the first width C1 and spaced apart from the fifth light reception structure 831 by the second width C2. The fifth light reception structure 831, the sixth light reception structure 832, the seventh light reception structure 833, and the eighth light reception structure 834 may configure the shape obtained by dividing a ring, having a first radius R2 as the inner radius and a second radius R3 as the outer radius, into four pieces.

Figure 8C:
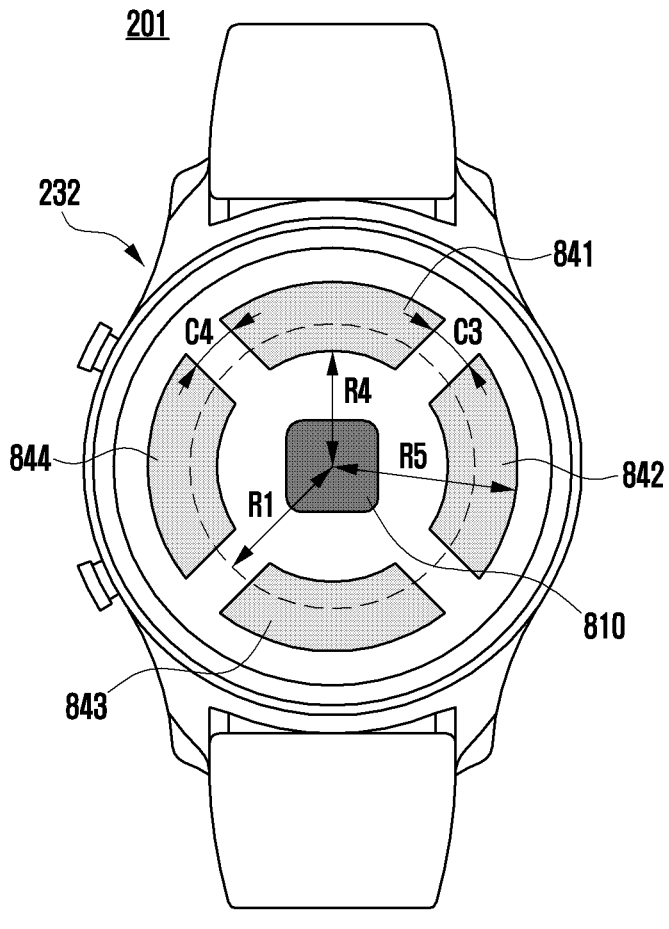
FIG. 8C is a diagram illustrating a light output structure and a light reception structure disposed on a second surface or rear surface of an electronic device according to an embodiment of the disclosure.

FIG. 8C is a diagram illustrating a light output structure and a light reception structure disposed on the second surface or the rear surface 232 of the electronic device 201 according to an embodiment of the disclosure.

In an embodiment, an electronic device 201 may include a light output structure 810 and a plurality of light reception structures 841, 842, 843, and 844 on a second surface 232. The light output structure 810 may include an output coupler 315 in at least a part thereof. The electronic device 201 may include the plurality of light reception structures 841, 842, 843, and 844 spaced a first distance R1 apart from the light output structure 810 at the center. The first distance R1 may have a specified length. Each of the plurality of light reception structures 841, 842, 843, and 844 may include a reception circuit 330 and/or a photo detector.

Referring to FIG. 8C, the ninth light reception structure 841, the tenth light reception structure 842, the eleventh light reception structure 843, and the twelfth light reception structure 844 may be disposed around the light output structure 810 as the center.

In an embodiment, the ninth light reception structure 841 may be spaced apart from the tenth light reception structure 842 by a third width C3 and spaced apart from the twelfth light reception structure 844 by a fourth width C4. The tenth light reception structure 842 may be spaced apart from the ninth light reception structure 841 by the third width C3 and spaced apart from the eleventh light reception structure 843 by the fourth width C4. The eleventh light reception structure 843 may be spaced apart from the tenth light reception structure 842 by the fourth width C4 and spaced apart from the twelfth light reception structure 844 by the third width C3. The twelfth light reception structure 844 may be spaced apart from the eleventh light reception structure 843 by the third width C3 and spaced apart from the ninth light reception structure 841 by the fourth width C4. The ninth light reception structure 841, the tenth light reception structure 842, the eleventh light reception structure 843, and the twelfth light reception structure 844 may configure the shape obtained by dividing a ring, having a fourth radius R4 as the inner radius and a fifth radius R5 as the outer radius, into four pieces.

Referring to FIGS. 8B and 8C, the arrangement of the ninth light reception structure 841, the tenth light reception structure 842, the eleventh light reception structure 843, and the twelfth light reception structure 844 in FIG. 8C may be obtained by rotating the arrangement of the fifth light reception structure 831, the sixth light reception structure 832, the seventh light reception structure 833, and the eighth light reception structure 834 at about 45 degrees around the light output structure 810.

Figure 8D:
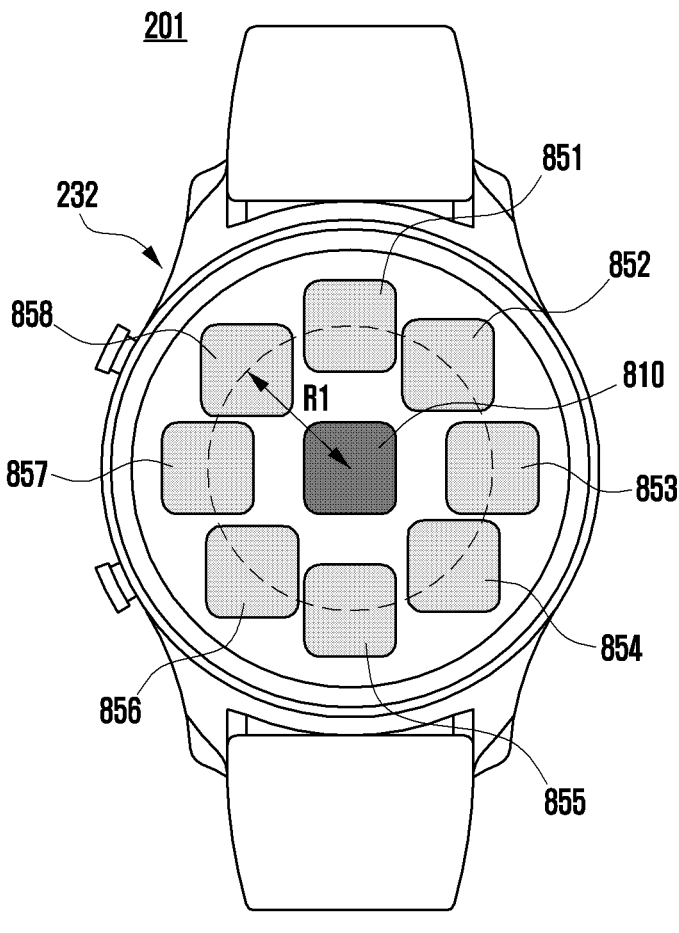
FIG. 8D is a diagram illustrating a light output structure and a light reception structure disposed on a second surface or rear surface of an electronic device according to an embodiment of the disclosure.

FIG. 8D is a diagram illustrating a light output structure and a light reception structure disposed on the second surface or the rear surface 232 of the electronic device 201 according to an embodiment of the disclosure.

In an embodiment, an electronic device 201 may include a light output structure 810 and a plurality of light reception structures 851, 852, 853, 854, 855, 856, 857, and 858 on a second surface 232. The light output structure 810 may include an output coupler 315 in at least a part thereof. The electronic device 201 may include the plurality of light reception structures 851, 852, 853, 854, 855, 856, 857, and 858 spaced a first distance R1 apart from the light output structure 810 at the center. The first distance R1 may have a specified length. Each of the plurality of light reception structures 851, 852, 853, 854, 855, 856, 857, and 858 may include a reception circuit 330 and/or a photo detector.

Referring to FIG. 8D, the 13th light reception structure 851, the 15th light reception structure 853, the 17th light reception structure 855, and the 19th light reception structure 857 be disposed in the shape of a cross, based on the light output structure 810. The 14th light reception structure 352 may be disposed between the 13th light reception structure 851 and the 15th light reception structure 853. The 16th light reception structure 354 may be disposed between the 15th light reception structure 853 and the 17th light reception structure 855. The 18th light reception structure 856 may be disposed between the 17th light reception structure 855 and the 19th light reception structure 857. The 20th light reception structure 858 may be disposed between the 19th light reception structure 857 and the 13th light reception structure 851.

In an embodiment, the 13th light reception structure 851, the 14th light reception structure 352, the 15th light reception structure 853, the 16th light reception structure 354, and the 17th light reception structure 855, the 18th light reception structure 856, the 19th light reception structure 857, and the 20th light reception structure 858 may have a rectangular shape having substantially the same size.

Figure 8E:
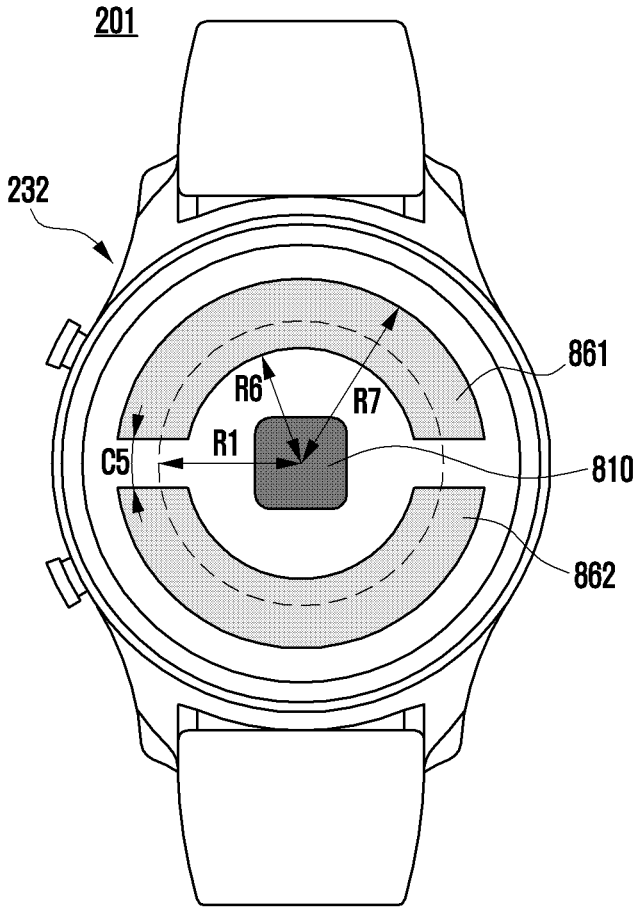
FIG. 8E is a diagram illustrating a light output structure and a light reception structure disposed on a second surface or rear surface of an electronic device according to an embodiment of the disclosure.

FIG. 8E is a diagram illustrating a light output structure and a light reception structure disposed on the second surface or the rear surface 232 of the electronic device 201 according to an embodiment of the disclosure.

In an embodiment, an electronic device 201 may include a light output structure 810 and a plurality of light reception structures 861 and 862 on a second surface 232. The light output structure 810 may include an output coupler 315 in at least a part thereof. The electronic device 201 may include the plurality of light reception structures 861 and 862 spaced a first distance R1 apart from the light output structure 810 at the center. The first distance R1 may have a specified length. Each of the plurality of light reception structures 861 and 862 may include a reception circuit 330 and/or a photo detector.

Referring to FIG. 8E, the 21st light reception structure 861 and the 22nd light reception structure 862 may be disposed around the light output structure 810.

In an embodiment, the 21st light reception structure 861 and the 22nd light reception structure 862 may be spaced apart from each other by a fifth width C5. The 21st light reception structure 861 and the 22nd light reception structure 862 may configure the shape obtained by dividing a ring, having a sixth radius R6 as the inner radius and a seventh radius R7 as the outer radius, into two pieces.

Figure 8F:
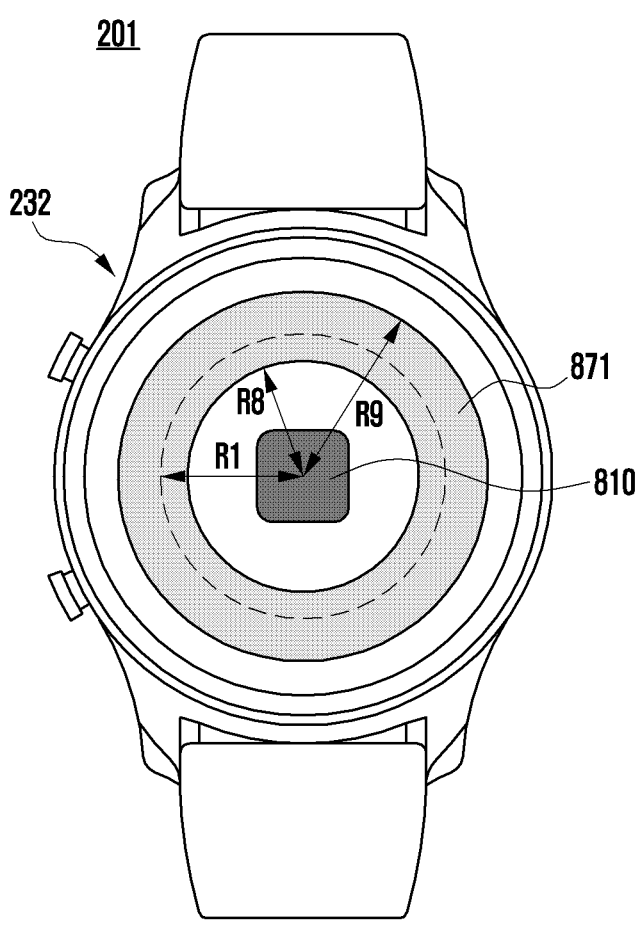
FIG. 8F is a diagram illustrating a light output structure and a light reception structure disposed on a second surface or rear surface of an electronic device according to an embodiment of the disclosure.

FIG. 8F is a diagram illustrating a light output structure and a light reception structure disposed on the second surface or the rear surface 232 of the electronic device 201 according to an embodiment of the disclosure.

In an embodiment, an electronic device 201 may include a light output structure 810 and at least one light reception structure 871 on a second surface 232. The light output structure 810 may include an output coupler 315 in at least a part thereof. The electronic device 201 may include a 23rd light reception structure 871 spaced a first distance R1 apart from the light output structure 810 at the center. The first distance R1 may have a specified length. The 23rd light reception structure 871 may include a reception circuit 330 and/or a photo detector. The 23rd light reception structure 871 may have a ring shape with an eighth radius R8 as the inner radius and a ninth radius R9 as the outer radius.

Figure 8G:
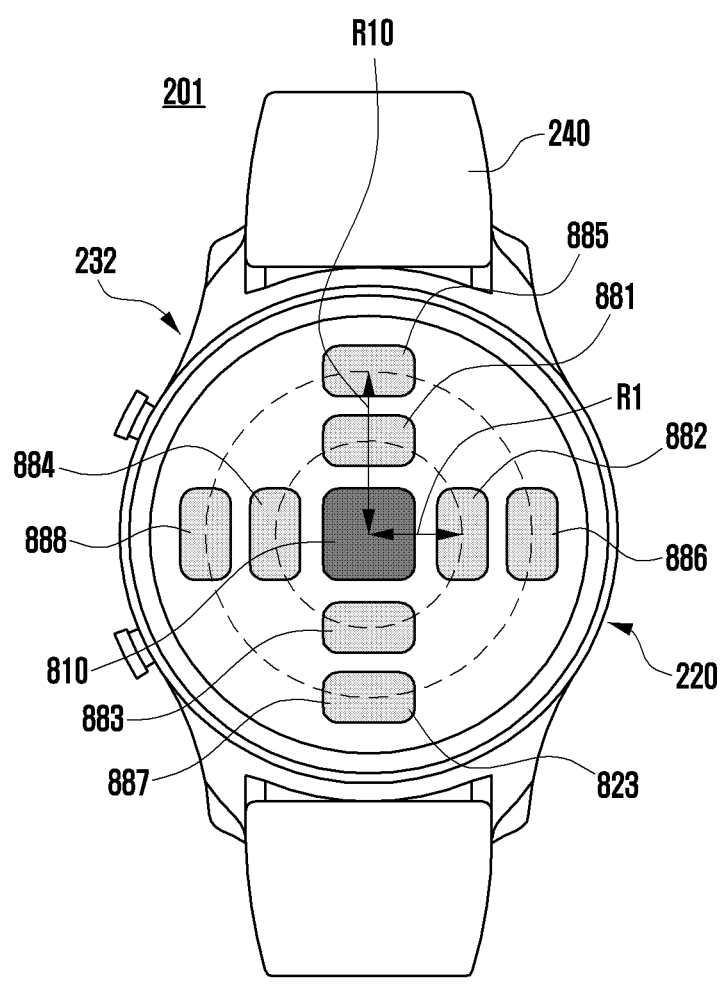
FIG. 8G is a diagram illustrating a light output structure and a light reception structure disposed on a second surface or rear surface of an electronic device according to an embodiment of the disclosure.

FIG. 8G is a diagram illustrating a light output structure and a light reception structure disposed on the second surface or the rear surface 232 of the electronic device 201 according to an embodiment of the disclosure.

In an embodiment, an electronic device 201 may include a light output structure 810 and a plurality of light reception structures 881, 882, 883, 884, 885, 886, 887, and 888 on a second surface 232. The light output structure 810 may include an output coupler 315 in at least a part thereof. The electronic device 201 may include the plurality of first light reception structures 881, 882, 883, and 884 spaced a first distance R1 apart from the light output structure 810 at the center. The first distance R1 may have a specified length.

In an embodiment, the electronic device 201 may include a plurality of second light reception structures 885, 886, 887, and 888 spaced a second distance R10 apart from the light output structure 810 at the center. The second distance R10 may have a specified length. The second distance R10 may be greater than the first distance R1 from the center of the light output structure 810. The second distance R10 may be longer than the first distance R1.

In an embodiment, since the plurality of first light reception structures 881, 882, 883, and 884 and the plurality of second light reception structures 885, 886, 887, and 888 receive light at different distances from the light output structure 810, they may receive light with different depths of penetration into the user's body.

In an embodiment, each of the plurality of light reception structures 881, 882, 883, 884, 885, 886, 887, and 888 may include a reception circuit 330 and/or a photo detector.

Referring to FIG. 8G, the 24th light reception structure 881, the 25th light reception structure 882, the 26th light reception structure 883, the 27th light reception structure 884, the 28th light reception structure 885, the 29th light reception structure 886, the 30th light reception structure 887, and the 31st light reception structure 888 may be disposed in the shape of a cross, based on the light output structure 810. The 24th light reception structure 881, the 25th light reception structure 882, the 26th light reception structure 883, the 27th light reception structure 884, the 28th light reception structure 885, the 29th light reception structure 886, the 30th light reception structure 887, and the 31st light reception structure 888 may have a rectangular shape with substantially the same size.

Figure 8H:
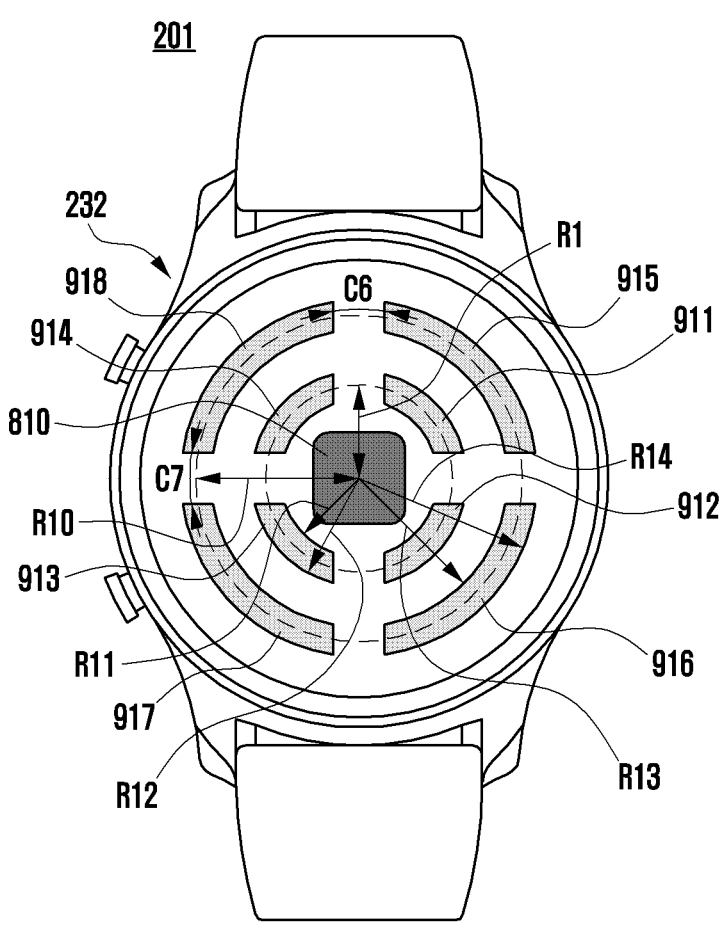
FIG. 8H is a diagram illustrating a light output structure and a light reception structure disposed on a second surface or rear surface of an electronic device according to an embodiment of the disclosure.

FIG. 8H is a diagram illustrating a light output structure and a light reception structure disposed on the second surface or the rear surface 232 of the electronic device 201 according to an embodiment of the disclosure.

In an embodiment, an electronic device 201 may include a light output structure 810 and a plurality of light reception structures 911, 912, 913, 914, 915, 916, 917, and 918 on a second surface 232. The light output structure 810 may include an output coupler 315 in at least a part thereof. The electronic device 201 may include the plurality of third light reception structures 911, 912, 913, and 914 spaced a first distance R1 apart from the light output structure 810 at the center. The first distance R1 may have a specified length.

In an embodiment, the electronic device 201 may include a plurality of fourth light reception structures 915, 916, 917, and 918 spaced a second distance R10 apart from the light output structure 810 at the center. The second distance R10 may have a specified length. The second distance R10 may be greater than the first distance R1 from the center of the light output structure 810. The second distance R10 may be longer than the first distance R1.

In an embodiment, each of the plurality of light reception structures 911, 912, 913, 914, 915, 916, 917, and 918 may include a reception circuit 330 and/or a photo detector.

Referring to FIG. 8H, the 32nd light reception structure 911, the 33rd light reception structure 912, the 34th light reception structure 913, the 35th light reception structure 914, the 36th light reception structure 915, the 37th light reception structure 916, the 38th light reception structure 917, and the 39th light reception structure 918 may be disposed around the light output structure 810 as the center.

In an embodiment, the 32nd light reception structure 911 may be spaced apart from the 33rd light reception structure 912 by a seventh width C7 and spaced apart from the 35th light reception structure 914 by a sixth width C6.

In an embodiment, the 33rd light reception structure 912 may be spaced apart from the 34th light reception structure 913 by the sixth width C6 and spaced apart from the 32nd light reception structure 911 by a seventh width C7.

In an embodiment, the 34th light reception structure 913 may be spaced apart from the 35th light reception structure 914 by the seventh width C7 and spaced apart from the 33rd light reception structure 912 by the sixth width C6.

In an embodiment, the 35th light reception structure 914 may be spaced apart from the 32nd light reception structure 911 by the sixth width C6 and spaced apart from the 34th light reception structure 913 by the seventh width C7.

In an embodiment, the 32nd light reception structure 911, the 33rd light reception structure 912, the 34th light reception structure 913, and the 35th light reception structure 914 may configure the shape obtained by dividing a ring, having an eleventh radius R11 as the inner radius and a twelfth radius R12 as the outer radius, into four pieces.

In an embodiment, the 36th light reception structure 915 may be spaced apart from the 37th light reception structure 916 by a seventh width C7 and spaced apart from the 39th light reception structure 918 by a sixth width C6.

In an embodiment, the 37th light reception structure 916 may be spaced apart from the 38th light reception structure 917 by the sixth width C6 and spaced apart from the 36th light reception structure 915 by the seventh width C7.

In an embodiment, the 38th light reception structure 917 may be spaced apart from the 39th light reception structure 918 by the seventh width C7 and spaced apart from the 37th light reception structure 916 by the sixth width C6.

In an embodiment, the 39th light reception structure 918 may be spaced apart from the 36th light reception structure 915 by the sixth width C6 and spaced apart from the 38th light reception structure 917 by the seventh width C7.

In an embodiment, the 36th light reception structure 915, the 37th light reception structure 916, the 38th light reception structure 917, and the 39th light reception structure 918 may configure the shape obtained by dividing a ring, having a 13th radius R13 as the inner radius and a 14th radius R14 as the outer radius, into four pieces. The 13th radius R13 may be greater than the 12th radius R12 from the light output structure 810. The 13th radius R13 may be longer than the 12th radius R12 from the center of the light output structure 810.

Figure 8I:
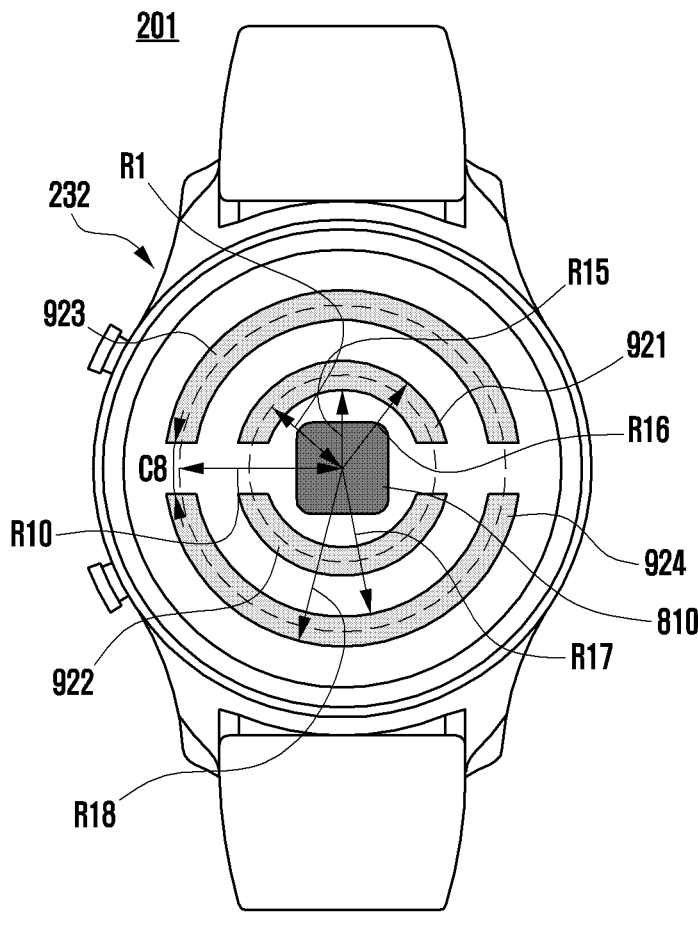
FIG. 8I is a diagram illustrating a light output structure and a light reception structure disposed on a second surface or rear surface of an electronic device according to an embodiment of the disclosure.

FIG. 8I is a diagram illustrating a light output structure and a light reception structure disposed on the second surface or the rear surface 232 of the electronic device 201 according to an embodiment of the disclosure.

In an embodiment, an electronic device 201 may include a light output structure 810 and a plurality of light reception structures 921, 922, 923, and 924 on a second surface 232. The light output structure 810 may include an output coupler 315 in at least a part thereof. The electronic device 201 may include a plurality of fifth light reception structures 921 and 922 spaced a first distance R1 apart from the light output structure 810 at the center. The first distance R1 may have a specified length.

In an embodiment, the electronic device 201 may include a plurality of sixth light reception structures 923 and 924 spaced a second distance R10 apart from the light output structure 810 at the center. The second distance R10 may have a specified length. The second distance R10 may be greater than the first distance R1 from the center of the light output structure 810. The second distance R10 may be longer than the first distance R1.

Referring to FIG. 8I, the 40th light reception structure 921, the 41st light reception structure 922, the 42nd light reception structure 923, and the 43rd light reception structure 924 may be disposed around the light output structure 810 as the center.

In an embodiment, the 40th light reception structure 921 and the 41st light reception structure 922 may be spaced apart by an eighth width C8. The 40th light reception structure 921 and the 41st light reception structure 922 may configure the shape obtained by dividing a ring, having a 15th radius R15 as the inner radius and a 16th radius R16 as the outer radius, into two pieces.

In an embodiment, the 42nd light reception structure 923 and the 43rd light reception structure 924 may be spaced apart by the eighth width C8. The 42nd light reception structure 923 and the 43rd light reception structure 924 may configure the shape obtained by dividing a ring, having a 17th radius R17 as the inner radius and an 18th radius R18 as the outer radius, into two pieces. The 17th radius R17 may be greater than the 16th radius R16 from the light output structure 810. The 17th radius R17 may be longer than the 16th radius R16 from the center.

In an embodiment, an electronic device (e.g., the electronic device 101 in FIG. 1 or the electronic device 201 in FIG. 2) may include a transmission circuit 310, a reception circuit 330, memory storing one or more computer programs, and one or more processors (e.g., the processor 120 in FIG. 1 or the processor 320 in FIG. 3) communicatively coupled to the transmission circuit, the reception circuit, and the memory.

In an embodiment, the transmission circuit 310 may include: a laser gain circuit 311 configured to output or generate a plurality of laser lights in a broadband under the control of the one or more processors (e.g., the processor 120 in FIG. 1 or the processor 320 in FIG. 3), a fixed array distributed Bragg reflector (DBR) grating 312 configured to change wavelengths of the plurality of laser lights and output a plurality of laser lights having specified wavelengths, a modulator 313 configured to modulate the plurality of laser lights having the specified wavelengths, a monitoring circuit 314 configured to identify whether or not the plurality of modulated laser lights is output in a specified intensity and specified wavelength, and an output coupler 315 configured to adjust output directions and/or angles of the plurality of modulated laser lights and output the plurality of modulated laser lights to the outside of the electronic device (e.g., the electronic device 101 in FIG. 1 or the electronic device 201 in FIG. 2).

In an embodiment, the reception circuit 330 may include at least one photo detector.

In an embodiment, the at least one photo detector may be spaced a specified distance apart from the output coupler 315.

In an embodiment, the laser gain circuit 311 may include a plurality of laser gain chips and output or generate the plurality of laser lights in a broadband in time division.

In an embodiment, the specified wavelength may be shorter than the wavelengths of the plurality of laser lights.

In an embodiment, the modulator 313 may modulate the plurality of laser lights having the specified wavelengths into continuous waves or pulse waves.

In an embodiment, the modulator 313 may include a lock-in amplifier and/or a low pass filter.

In an embodiment, the monitoring circuit 314 may include an edge illuminated photodiode, a Mach-Zehnder interferometer (MZI) sensor, a ring resonator, a line coupling, and/or a splitter.

In an embodiment, the monitoring circuit 314 may be disposed between and connected to the output coupler 315 and the modulator 313.

In an embodiment, in the electronic device (e.g., the electronic device 101 in FIG. 1 or the electronic device 201 in FIG. 2), the one or more processors (e.g., the processor 120 in FIG. 1 or the processor 320 in FIG. 3) may control time synchronization of the reception circuit 330 to receive the plurality of modulated laser lights in time division and/or sequence.

In an embodiment, the reception circuit 330 may include a plurality of photo detectors.

In an embodiment, in the electronic device (e.g., the electronic device 101 in FIG. 1 or the electronic device 201 in FIG. 2), each of the plurality of photo detectors may be spaced a first specified distance apart from the output coupler.

In an embodiment, each of the plurality of photo detectors of the reception circuit may be spaced a first specified distance or a second specified distance apart from the output coupler 315.

In an embodiment, the one or more processors (e.g., the processor 120 in FIG. 1 or the processor 320 in FIG. 3) may control the intensity and wavelength of light output from the laser gain circuit 311, based on information received from the monitoring circuit 314.

In an embodiment, the electronic device (e.g., the electronic device 101 in FIG. 1 or the electronic device 201 in FIG. 2) may include a case 220 having the transmission circuit 310 and the reception circuit 330 disposed on the rear surface thereof; a display disposed on the front surface of the case 220; and a band 240 connected to the case 220 and configured to enable the electronic device (e.g., the electronic device 101 in FIG. 1 or the electronic device 201 in FIG. 2) to be worn on the user's wrist.

In an embodiment, the rear surface of the case 220 is configured to at least partially come into contact with a user when the electronic device (e.g., the electronic device 101 in FIG. 1 or the electronic device 201 in FIG. 2) is worn on the user using the band 240.

In an embodiment, the rear surface of the case 220 may be configured such that at least a portion of the output coupler 315 and at least a portion of the reception circuit 330 are exposed.

In an embodiment, a method for controlling a sensor in an electronic device (e.g., the electronic device 101 in FIG. 1 or the electronic device 201 in FIG. 2) may include controlling a laser gain circuit 311 to output or generate a plurality of laser lights in a broadband, performing control to change wavelengths of the laser lights in a broadband, based on a fixed array DBR grating 312, and output a plurality of laser lights having specified wavelengths, modulating the plurality of laser lights having the specified wavelengths, identifying whether or not the plurality of modulated laser lights is output in a specified intensity and specified wavelength, adjusting output directions and/or angles of the plurality of modulated laser lights and outputting the same to the outside of the electronic device (e.g., the electronic device 101 in FIG. 1 or the electronic device 201 in FIG. 2), and detecting the plurality of modulated laser lights through a reception circuit 330.

In an embodiment, the sensor control method of the electronic device (e.g., the electronic device 101 in FIG. 1 or the electronic device 201 in FIG. 2) may include outputting or generating the plurality of laser lights in a broadband in time division.

In an embodiment, the sensor control method of the electronic device (e.g., the electronic device 101 in FIG. 1 or the electronic device 201 in FIG. 2) may include modulating the plurality of laser lights having the specified wavelengths into continuous waves or pulse waves.

In an embodiment, the sensor control method of the electronic device (e.g., the electronic device 101 in FIG. 1 or the electronic device 201 in FIG. 2) may include controlling time synchronization of the reception circuit 330 to receive the plurality of modulated laser lights in time division and/or sequence.

In another embodiment, an electronic device is provided. The electronic device includes a transmission circuit, a reception circuit, memory storing one or more computer programs, and one or more processors communicatively coupled to the transmission circuit, the reception circuit, and the memory, wherein the one or more computer programs include computer-executable instructions that, when executed by the one or more processors, cause the electronic device to control a laser gain circuit to output or generate a plurality of laser lights in a broadband, perform control to change wavelengths of the laser lights in a broadband, based on a fixed array DBR grating, and output a plurality of laser lights having specified wavelengths, modulate the plurality of laser lights having the specified wavelengths, identify whether or not the plurality of modulated laser lights is output in a specified intensity and specified wavelength, adjust output directions and/or angles of the plurality of modulated laser lights and outputting the same to the outside of the electronic device, and detect the plurality of modulated laser lights through a reception circuit.

In yet another embodiment, one or more non-transitory computer-readable storage media storing one or more computer programs including computer-executable instructions that, when executed by one or more processors of an electronic device, cause the electronic device to perform operations are provided. The operations include controlling a laser gain circuit to output or generate a plurality of laser lights in a broadband, performing control to change wavelengths of the laser lights in a broadband, based on a fixed array DBR grating, and output a plurality of laser lights having specified wavelengths, modulating the plurality of laser lights having the specified wavelengths, identifying whether or not the plurality of modulated laser lights is output in a specified intensity and specified wavelength, adjusting output directions and/or angles of the plurality of modulated laser lights and outputting the same to the outside of the electronic device, and detecting the plurality of modulated laser lights through a reception circuit.

The electronic device according to various embodiments disclosed herein may be one of various types of electronic devices. The electronic devices may include, for example, a portable communication device (e.g., a smart phone), a computer device, a portable multimedia device, a portable medical device, a camera, a wearable device, or a home appliance. The electronic device according to embodiments of the disclosure is not limited to those described above.

It should be appreciated that various embodiments of the disclosure and the terms used therein are not intended to limit the technological features set forth herein to particular embodiments and include various changes, equivalents, or alternatives for a corresponding embodiment. As used herein, each of such phrases as "A or B," "at least one of A and B," "at least one of A or B," "A, B, or C," "at least one of A, B, and C," and "at least one of A, B, or C," may include any one or all possible combinations of the items enumerated together in a corresponding one of the phrases. As used herein, such terms as "a first", "a second", "the first", and "the second" may be used to simply distinguish a corresponding element from another, and does not limit the elements in other aspect (e.g., importance or order). If an element (e.g., a first element) is referred to, with or without the term "operatively" or "communicatively", as "coupled with/to" or "connected with/to" another element (e.g., a second element), it means that the element may be coupled/connected with/to the other element directly (e.g., wiredly), wirelessly, or via a third element.

As used in various embodiments of the disclosure, the term "module" may include a unit implemented in hardware, software, or firmware, and may be interchangeably used with other terms, for example, "logic," "logic block," "component," or "circuit". The "module" may be a single integrated component, or a minimum unit or part thereof, adapted to perform one or more functions. For example, according to an embodiment, the "module" may be implemented in the form of an application-specific integrated circuit (ASIC).

Various embodiments as set forth herein may be implemented as software (e.g., the program 140) including one or more instructions that are stored in a storage medium (e.g., the internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions each may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, methods according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each element (e.g., a module or a program) of the above-described elements may include a single entity or multiple entities, and some of the multiple entities may be separately disposed in any other element. According to various embodiments, one or more of the above-described elements or operations may be omitted, or one or more other elements or operations may be added. Alternatively or additionally, a plurality of elements (e.g., modules or programs) may be integrated into a single element. In such a case, according to various embodiments, the integrated element may still perform one or more functions of each of the plurality of elements in the same or similar manner as they are performed by a corresponding one of the plurality of elements before the integration. According to various embodiments, operations performed by the module, the program, or another element may be carried out sequentially, in parallel, repeatedly, or heuristically, or one or more of the operations may be executed in a different order or omitted, or one or more other operations may be added.

It will be appreciated that various embodiments of the disclosure according to the claims and description in the specification can be realized in the form of hardware, software or a combination of hardware and software.

Any such software may be stored in non-transitory computer readable storage media. The non-transitory computer readable storage media store one or more computer programs (software modules), the one or more computer programs include computer-executable instructions that, when executed by one or more processors of an electronic device, cause the electronic device to perform a method of the disclosure.

Any such software may be stored in the form of volatile or non-volatile storage such as, for example, a storage device like read only memory (ROM), whether erasable or rewritable or not, or in the form of memory such as, for example, random access memory (RAM), memory chips, device or integrated circuits or on an optically or magnetically readable medium such as, for example, a compact disk (CD), digital versatile disc (DVD), magnetic disk or magnetic tape or the like. It will be appreciated that the storage devices and storage media are various embodiments of non-transitory machine-readable storage that are suitable for storing a computer program or computer programs comprising instructions that, when executed, implement various embodiments of the disclosure. Accordingly, various embodiments provide a program comprising code for implementing apparatus or a method as claimed in any one of the claims of this specification and a non-transitory machine-readable storage storing such a program.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
a transmission circuit;
a reception circuit; and
one or more processors communicatively coupled to the transmission circuit, and the reception circuit,
wherein the transmission circuit comprises:
a laser gain circuit configured to output or generate a plurality of first laser beams in a broadband under control of the one or more processors,
a fixed array distributed bragg reflector (DBR) grating configured to change each of the plurality of first laser beams into a corresponding one of a plurality of second laser beams, wherein each of the plurality of second laser beams has a specified wavelength,
a modulator configured to modulate the plurality of second laser beams,
a monitoring circuit configured to identify whether the plurality of modulated laser beams are output at a specified intensity and the specified wavelength, and
an output coupler configured to adjust output directions and angles of the plurality of modulated laser beams and output the plurality of modulated laser beams to an outside of the electronic device.

2. The electronic device of claim 1,
wherein the reception circuit comprises at least one photo detector, and
wherein the at least one photo detector is spaced a specified distance apart from the output coupler.

3. The electronic device of claim 1,
wherein the laser gain circuit comprises a plurality of laser gain chips, and
wherein the laser gain circuit is configured to output or generate the plurality of first laser beams in time division.

4. The electronic device of claim 1, wherein the specified wavelength is shorter than a wavelength of the plurality of first laser beams output from the laser gain circuit.

5. The electronic device of claim 1, wherein the modulator is configured to modulate the plurality of second laser beams into continuous waves or pulse waves.

6. The electronic device of claim 1, wherein the modulator comprises at least one of a lock-in amplifier or a low pass filter.

7. The electronic device of claim 1, wherein the monitoring circuit comprises at least one of an edge illuminated photodiode, a Mach-Zehnder interferometer (MZI) sensor, a ring resonator, a line coupling, or a splitter.

8. The electronic device of claim 1,
wherein the monitoring circuit is disposed between the output coupler and the modulator, and
wherein the monitoring circuit is connected to the output coupler and to the modulator.

9. The electronic device of claim 1, wherein the one or more processors are configured to control time synchronization of the reception circuit to receive the plurality of modulated laser beams in at least one of time division or sequence.

10. The electronic device of claim 1,
wherein the reception circuit comprises a plurality of photo detectors, and
wherein each of the plurality of photo detectors is spaced a first specified distance apart from the output coupler.

11. The electronic device of claim 10, wherein each of the plurality of photo detectors is spaced a first specified distance or a second specified distance apart from the output coupler.

12. The electronic device of claim 1, wherein the one or more processors are configured to control intensity and wavelength of light output from the laser gain circuit, based on information received from the monitoring circuit.

13. The electronic device of claim 1, further comprising:
a case having the transmission circuit and the reception circuit disposed on a rear surface thereof;
a display disposed on a front surface of the case; and
a band connected to the case and configured to enable the electronic device to be worn on a user's wrist.

14. The electronic device of claim 13, wherein the rear surface of the case is configured to at least partially come into contact with a user when the electronic device is worn on the user's wrist through the band.

15. The electronic device of claim 14, wherein the rear surface of the case is configured such that at least a portion of the output coupler and at least a portion of the reception circuit are exposed.

16. A method performed by an electronic device for controlling a sensor in the electronic device, the method comprising:

controlling, by the electronic device, a laser gain circuit to output or generate a plurality of first laser beams in a broadband;

performing, by the electronic device, control to change each of the plurality of first laser beams into a corresponding one of a plurality of second laser beams, wherein each of the plurality of second laser beams has a specified wavelength based on a fixed array distributed bragg reflector (DBR) grating;

modulating, by the electronic device, the plurality of second laser beams;

identifying, by the electronic device, whether the plurality of modulated laser beams are output at a specified intensity and the specified wavelength;

adjusting, by the electronic device, output directions and angles of the plurality of modulated laser beams and outputting the plurality of modulated laser beams to an outside of the electronic device; and detecting, by the electronic device the plurality of modulated laser beams through a reception circuit.

17. The method of claim 16, wherein the controlling of the laser gain circuit to output or generate the plurality of first laser beams comprises outputting or generating the plurality of first laser beams in time division.

18. The method of claim 16, wherein the specified wavelength is shorter than a wavelength of the plurality of first laser beams output from the laser gain circuit.

19. The method of claim 16, wherein the modulating of the plurality of second laser beams comprises modulating the plurality of second laser beams into continuous waves or pulse waves.

20. The method of claim 16, wherein the detecting of the plurality of modulated laser beams through the reception circuit comprises controlling time synchronization of the reception circuit to receive the plurality of modulated laser beams in at least one of time division or sequence.

* * * * *